US006265542B1

(12) United States Patent
Fahrner et al.

(10) Patent No.: US 6,265,542 B1
(45) Date of Patent: Jul. 24, 2001

(54) PURIFICATION OF MOLECULES

(75) Inventors: Robert Lee Fahrner, San Francisco; David Reifsnyder, El Cerrito, both of CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 09/168,548

(22) Filed: Oct. 8, 1998

Related U.S. Application Data
(60) Provisional application No. 60/063,119, filed on Oct. 24, 1997.

(51) Int. Cl.[7] .................. C07K 1/14; C07K 1/16
(52) U.S. Cl. .......... 530/344; 530/412; 530/415; 530/416; 210/656
(58) Field of Search .................. 530/344, 412, 530/415, 416; 210/656

(56) References Cited

U.S. PATENT DOCUMENTS

| | | | |
|---|---|---|---|
| 4,511,503 | 4/1985 | Olson et al. | 49/495 |
| 4,565,785 | 1/1986 | Gilbert et al. | 260/112 R |
| 4,617,378 | * 10/1986 | Rubinstein et al. | 530/351 |
| 4,673,641 | 6/1987 | George et al. | 435/172.3 |
| 4,710,473 | 12/1987 | Morris | 435/68 |
| 4,738,921 | 4/1988 | Belagaje et al. | 435/68 |
| 4,795,706 | 1/1989 | Helung et al. | 435/68 |
| 4,948,787 | * 8/1990 | Chen et al. | 514/141 |
| 5,256,294 | 10/1993 | Van Reis | 210/637 |
| 5,407,810 | 4/1995 | Builder et al. | 435/804 |
| 5,446,024 | * 8/1995 | Builder et al. | 514/12 |
| 5,451,660 | 9/1995 | Builder et al. | 530/344 |
| 5,459,052 | * 10/1995 | Skriver et al. | 435/71.2 |
| 5,490,937 | 2/1996 | Van Reis | 210/637 |
| 5,663,304 | 9/1997 | Builder et al. | 530/399 |
| 5,681,814 | 10/1997 | Clark et al. | 514/12 |

FOREIGN PATENT DOCUMENTS

| | | |
|---|---|---|
| WO 86/04486 | 8/1986 | (WO) . |
| WO 95/16777 | 6/1995 | (WO) . |

OTHER PUBLICATIONS

Roe, S. 'Separation based on structure.' In: Protein Purification Methods a Practical Approach. Edited by E. L. V. Harris and S. Angal. Oxford: IRL Press, 1989, pp. 230–232, 1989.*
Antia and Horvath. "High–performance liquid chromatography at elevated temperatures. examination of conditions for the rapid separation of large molecules" *J. Chromatography* 435:1–15 (1988).
Buckle et al., "Simultaneous separation of oestrogens and prostaglandins on an automated column chromatography system using Sephadex LH 20" *J. Physiol* 242(2):56P–57P (1974).
Canova–Davis et al., "Chemical heterogeneity as a result of hydroxylamine cleavage of a fusion protein of human insulin–like growth factor I" *Biochemical Journal* 285:207–213 (1992).
Chen and Horvath, "Rapid Separation of Proteins by Reversed Phase HPLC at Elevated Temperatures" *Analytical Methods and Instrumentation* 1(4):213–222 (1993).
Chen et al , "High–speed high–performance liquid chromatogrpahy of peptides and proteins" *J Chromat* 705:3–20 (1995).
Cornell et al., "Application of preparative reversed–phase high–performance liquid chromatography to isolation of insulin–like growth factor II from human serum" *J. Chromatography* 421:61–69 (1987).
Cornell HJ et al., "Isolation of insulin–like growth Factors I and II from human plasma" *Preparative Biochemistry* 14(2):123–138 (1984).
Cox and Snyder, "Preparative– and process–scale HPLC" *LC–GC* 6(10) , 894–909 (1988).
Dwyer, "High performance liquid chromatography as a process tool" *Recent Advances in Separation Techniques III* 83(250):130–127 (1986).Levison
Forsberg et al., "Separation and characterization of modified variants of recombinant human insulin–I growth factor I derived from a fusion protein secreted from *Escherichia coli*" *Biochemical Journal* 271:357–363 (1990).
Francis et al., "Sheep insulin–like growth factors I and II: Sequences, activities and assays" *Endocrinology* 134(3):1173–1183 (1989).
Geng et al . "Retention model for proteins in reversed–phase liquid chromatography" *J. Chromatography* 296:15–30 (1984).
Godbille et al., "Description and performance of an 8 cm i.d. column for preparative scale high pressure liquid–solid chromatography" *J. Chromatographic Science* 12:564–569 (Oct. 1974).
Guiochon et al . "Consolidation of particle beds and packing of chromatographic columns" *J. Chromatog. A* 762–83–88 (1997).
Hart et al., "Large Scale, In Situ Isolation of Periplasmic IGF–I from *E. coli*" *Bio/Technology* 12:1113–1117 (Nov. 1994).
Hartmanis et al., "Occurrence of Methionine Sulfoxide During Production of Recombinant Human Insulin–Like Growth Factor I (IGF–1)" *Techniques in Protein Chemistry* pp. 327–333 (1989).

(List continued on next page.)

Primary Examiner—Christopher S. F. Low
Assistant Examiner—Anish Gupta
(74) *Attorney, Agent, or Firm*—Janet E. Hasak

(57) ABSTRACT

A process for purifying molecules from contaminants is provided. In this process a mixture containing the molecule (peptide, polypeptide, or biologically active non-peptidyl compound) and its contaminants is loaded onto a reversed-phase liquid chromatography column and the molecule is eluted from the column with a buffer containing hexylene glycol.

15 Claims, 12 Drawing Sheets

OTHER PUBLICATIONS

Hodges et al., "Multi–column preparative reversed–phase sample displacement chromatography of peptides" *J. Chromatography* 548:267–280 (1991).

Jandera et al., "Effects of the gradient profile on the production rate in reversed–phase gradient elution overloaded chromatography" *J. Chromatog. A* 760:25–39 (1997).

Kennedy, "Ion–Exchange Chromatography of Proteins" *Methods Mol. Biol.* Chapter 16, 11:249–258 (1992).

Kroeff et al . "Production scale purification of biosynthetic human insulin by reversed–phase high–performance liquid chromatography" *J. Chromatography* 461:45–61 (1989).

Lee et al., "Preparative HPLC" *8th International Biotechnology Symposium—Proceedings* 1:593–610 (1988).

Lee et al., "Tandem separation schemes for preparative high–performance liquid chromatography of proteins" *J. Chromat* 443:31–43 (1988).

Levison et al., "Influence of flow–rate on the chromatographic performance of agarose– and cellulose–based anion–exchange media" *J. Chromatogr A* 734:137–143 (1996).

Li et al , "Selective protein separations using Formed–In–Place anion exchange membranes" *J. Biotechnol* 26:203–211 (1992).

Linde et al., "Non–ideal behaviour of silica–based stationary phases in trifluoroacetic acid–acetonitrile–based reversed–phase high–performance liquid chromatographic separations of insulins and proinsulins" *J Chromatogr* 536:43–55 (1991).

McDonald and Bidlingmeyer, "Strategies for Successful Preparative Liquid Chromatography" *Preparative Liquid Chromatography*, Brian A. Bidlingmeyer, New York: Elsevier Science Publishing vol. 38:1–104 (1987).

Nice et al., "Comparison of short and ultrashort–chain alkylsilane–bonded silicae for the high–performance liquid chromatography of proteins by hydrophobic interaction methods" *J Chromatrogr* 218:569–580 (1981).

Olson et al., "Preparative isolation of recombinant human insulin–like growth factor 1 by reversed–phase high–performance liquid chromatography" *J Chromatography A* 675:101–113 (1994).

Petrides et al., An improved method for the purification of human insulin–like growth factors I and II *Endocrinology* 118(5):2034–2038 (1986).

Qin et al., "Rates of Carbamylation of Specific Lysyl Residues in Bovine α–Crystallins" *Journal of Biological Chemistry* 267(36).26128–26133 (Dec. 25, 1992).

Raschdorf et al., "Location of disulphide bonds in human insulin–like growth factors (IGFs) synthesized by recombinant DNA technology" *Biomedical and Environmental Mass Spectrometry* 16:3–8 (1988).

Rinderknecht and Rumbel. "The amino acid sequence of human insulin–like growth factor I and its structural homology with proinsulin" *Journal of Biological Chemistry* 353(8):2769–2776 (1978).

Rinderknecht and Rumbel, "Polypeptides with nonsuppressible insulin–like and cell–growth promoting activities in human serum isolation, chemical characterization, and some biological properties of I and II" *Proc Natl Acad. Sci USA* 73(7):2365–2369 (1976).

Roe, S., "Separation based on structure" *Protein Purification Methods: a Practical Approach*, E L V. Harris and S. Angal eds., Oxford:IRL Press pp. 230–232 (1989).

Sadek *The HPLC Solvent Guide*, John Wiley & Sons, Inc. pp. 24–97, 204–210 and 227–265 (1996).

Sands et al., "Characterization of Bonded–Phase Silica Gels with Different Pure Diameters" *J Chromatogr* 360.353–369 (1986).

Sarker et al., "Study of the operating conditions of axial compression columns for preparative chromatography" *J Chromatography A* 709,227–259 (1995).

Snyder et al. *Practical HPLC Method Development*, New York,John Wiley & Sons pp. 1–51, 92–197, 227–251 (1988).

Snyder et al., "Cradient Eletion in Reversed–Phase HPLC Separation of Macromolecules" *Analytical Chemistry* 55(14)–1412A–1430A (Dec. 1983).

Stadalies et al. "Optimization model for the gradient elution separation of peptide mixtures by reversed–phase high–performance liquid chromatography. Application to methoc development and the choice of column configuration" *Journal of Chromatography* 327:93–113 (1985).

Stanley et al., "Consolidation of the packing material in chromatographic columns under dynamic axial compression IV. Mechanical properties of some packing materials" *J Chromatography A* 741 175–184 (1996).

Svoboda et al., "Purification of Somatomedin–C from Human Plasma: Chemical and Biological Properties, Partial Sequence Analysis, and Relationship to Other Somatomedins" *Biochemistry* 19 790–797 (1980).

Tan et al . "Revisionist look at solvophobic driving forces in reversed–phase liquid chromatography II Partitioning vs. adsorption mechanism in monomeric alkyl bonded phase supports" *J Chromatography A* 775:1–12 (1997).

Wei et al., "Optimization of an isocratic reversed phase liquid chromatographic system for the separation of fourteen steroids using factorial design and computer simulation" *Biomed. Chromatogr* 4(1):34–38 (1990).

Yang et al., "Factors affecting the separation and loading capacity of proteins in preparative gradient elution highperformance liquid chromatography" *J. Chromatog* 590:35–47 (1992).

Gulewicz et al., "A new approach to the crystallization of proteins" *FEBS Letters* 189(2):179–182 (Sep. 23, 1985).

\* cited by examiner

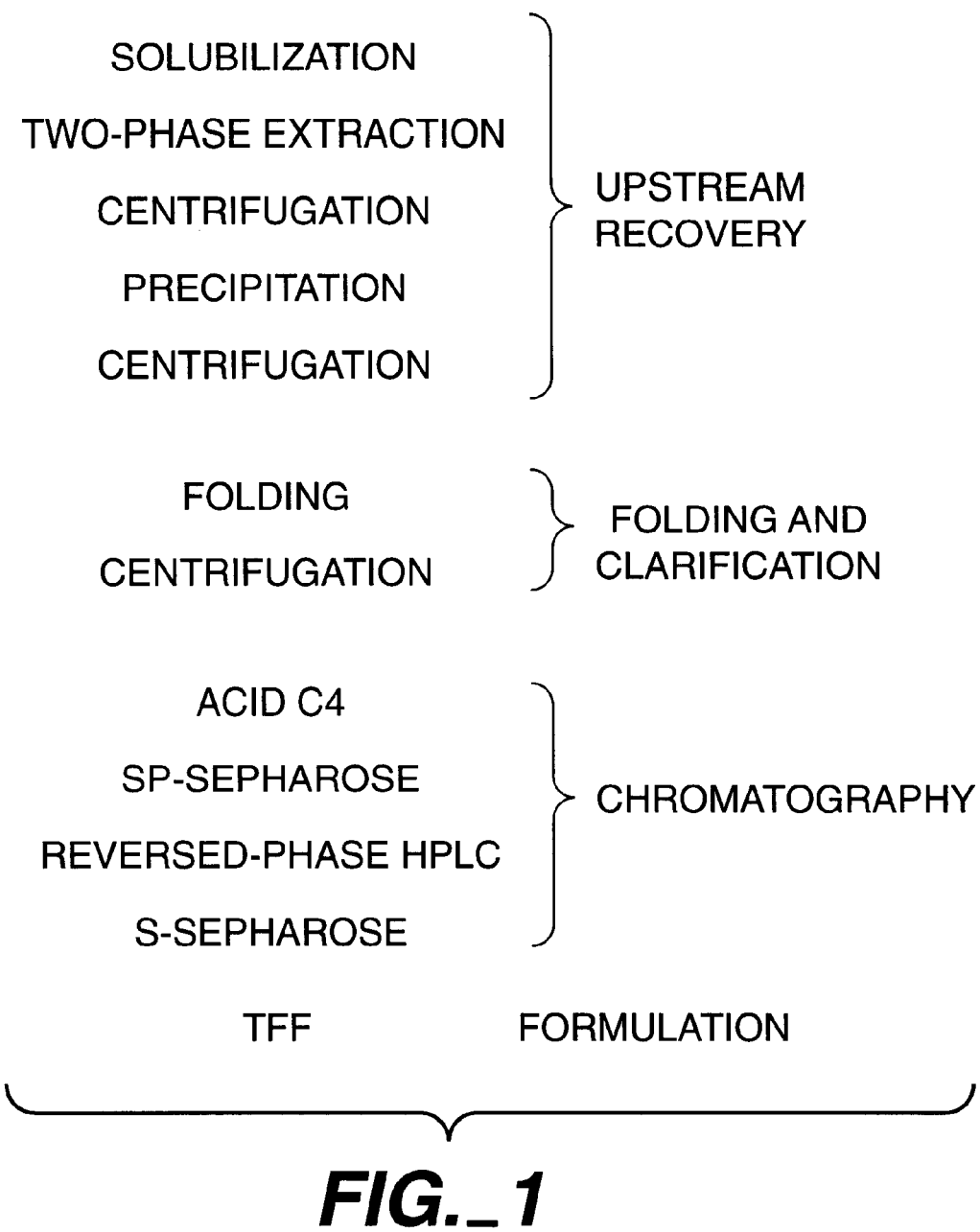
FIG._1

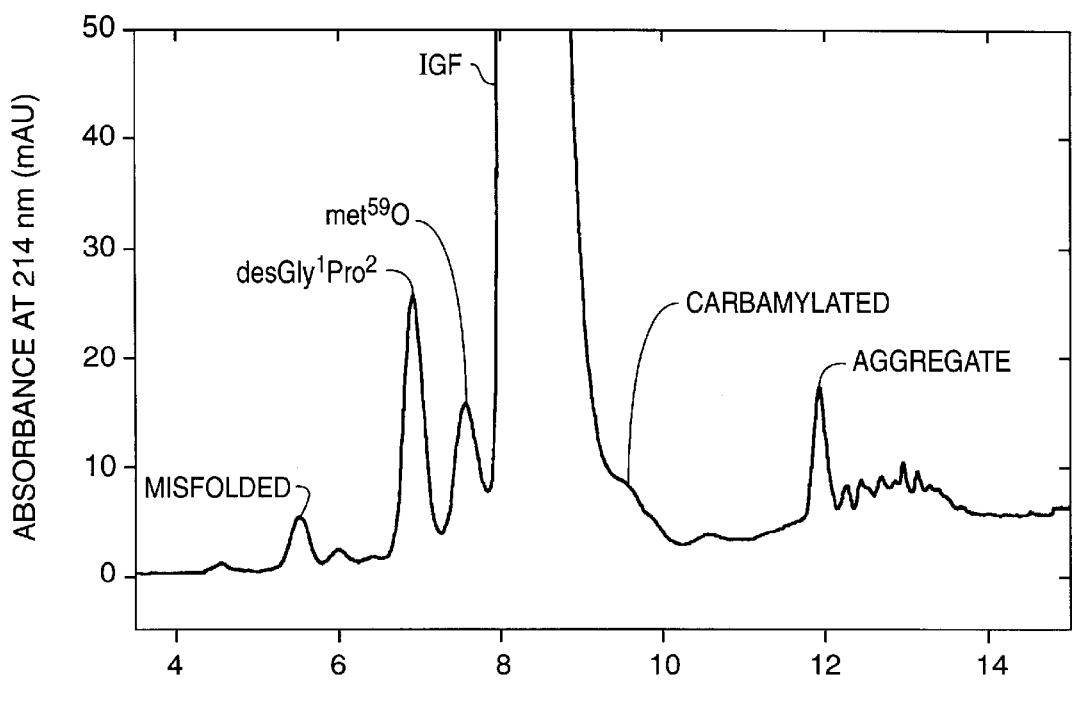
FIG._2
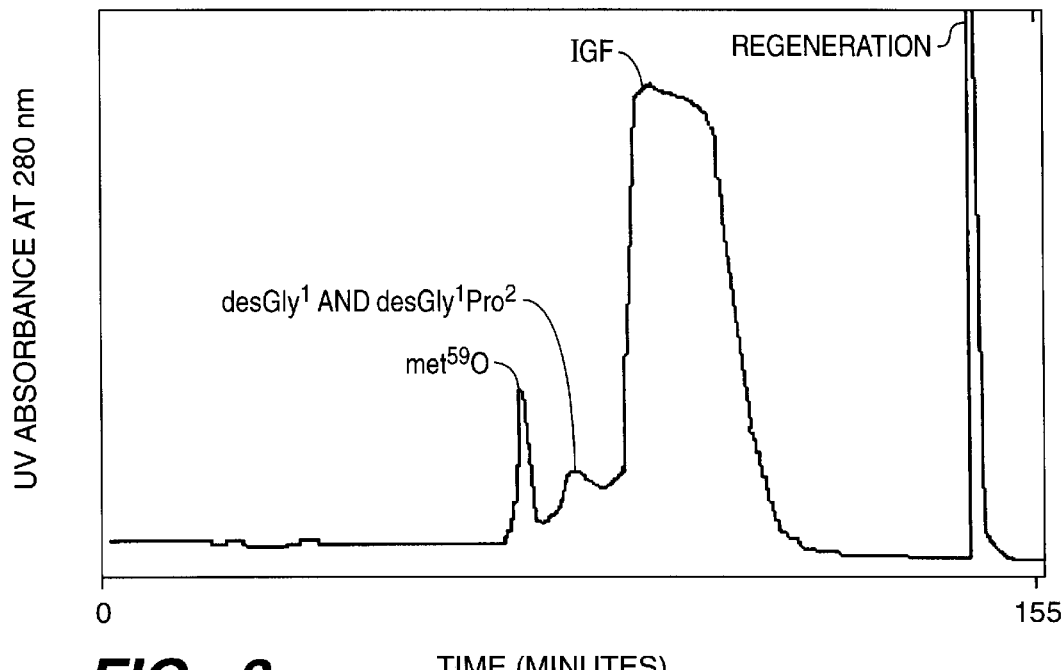
FIG._3

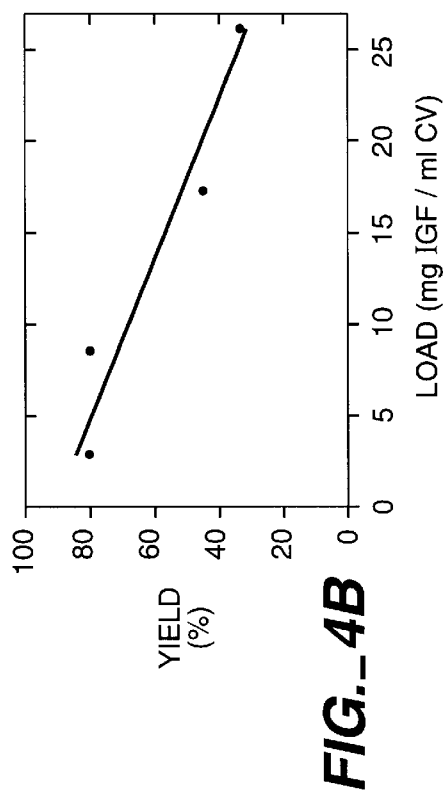
*FIG._4B*
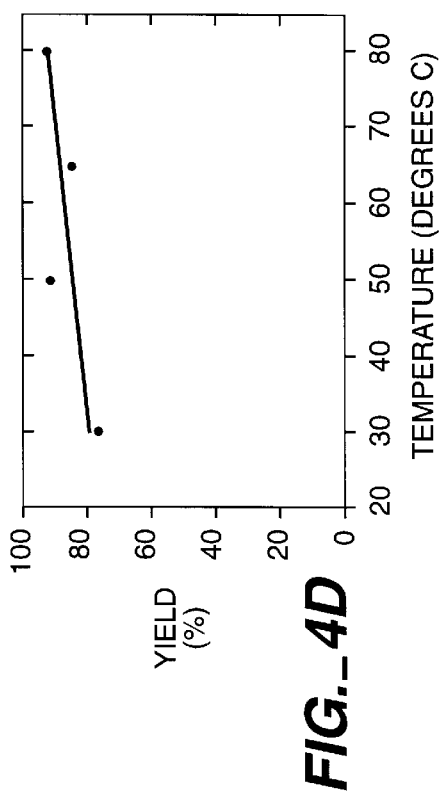
*FIG._4D*
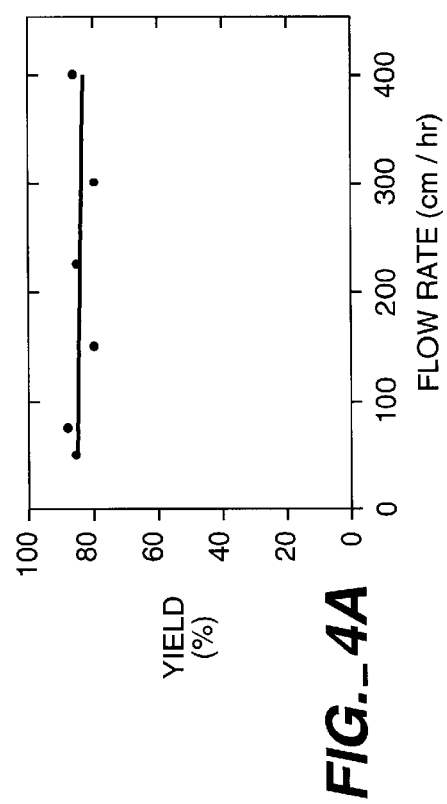
*FIG._4A*
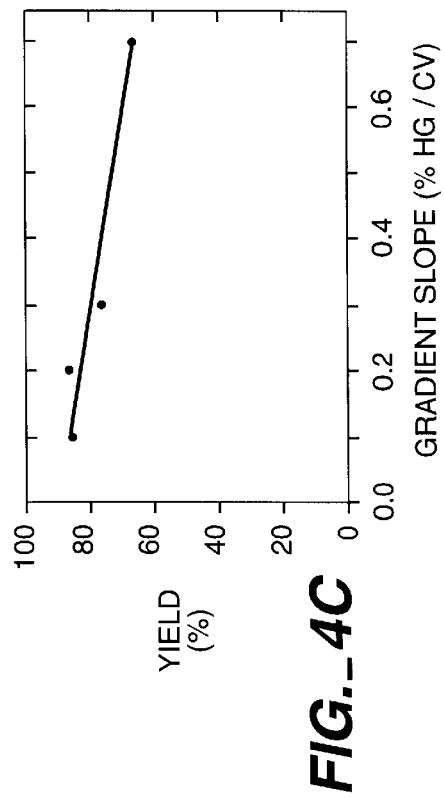
*FIG._4C*

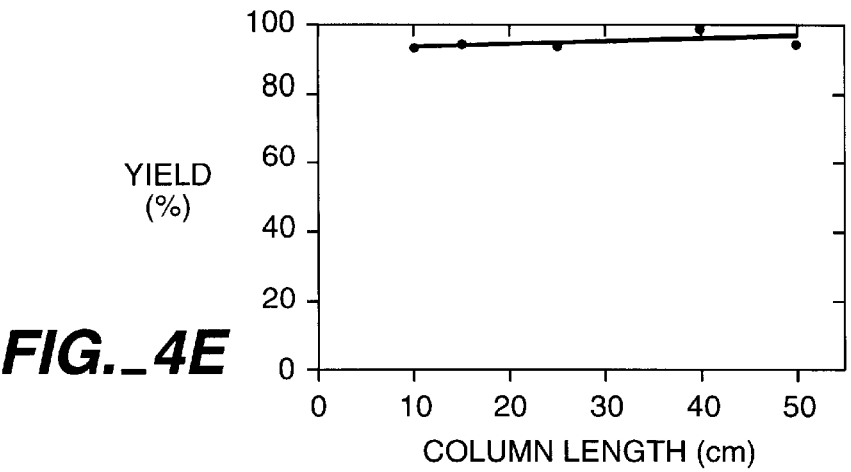
FIG._4E
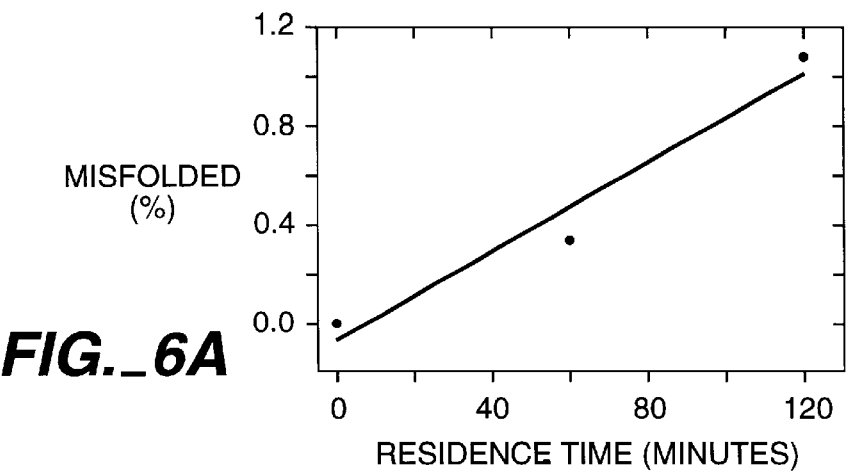
FIG._6A
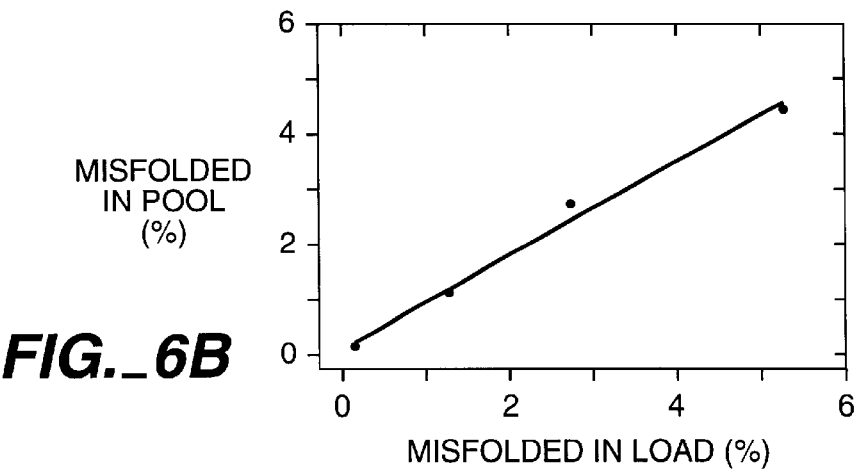
FIG._6B

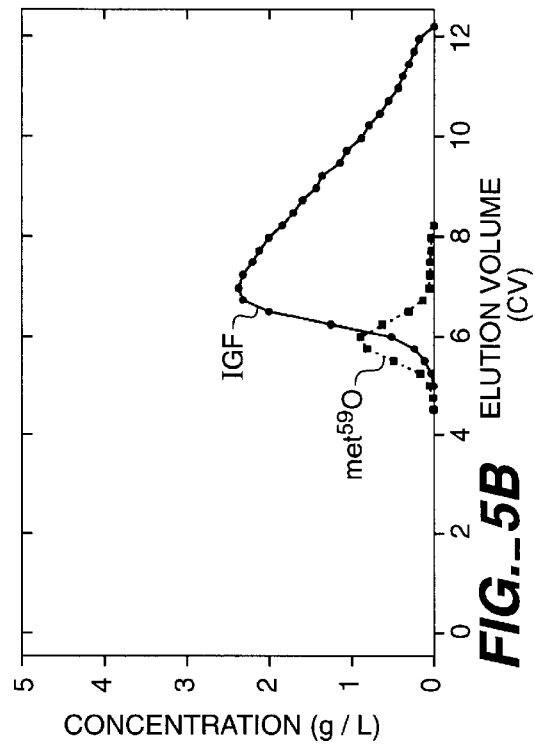
FIG._5A
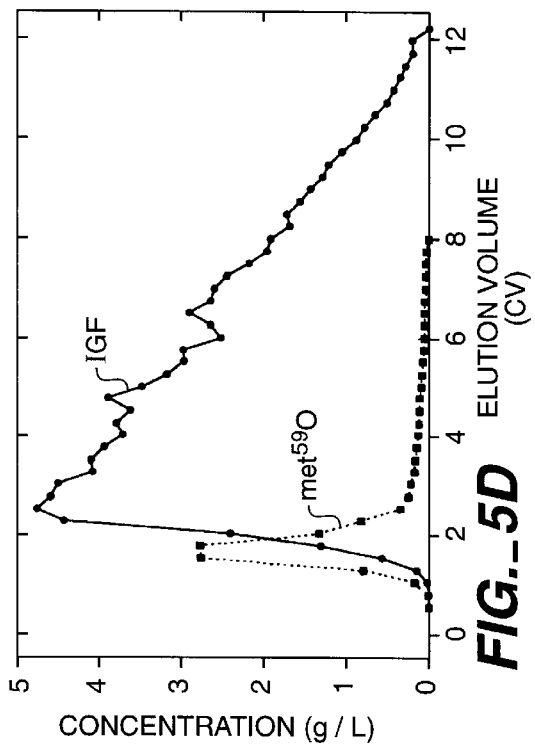
FIG._5B
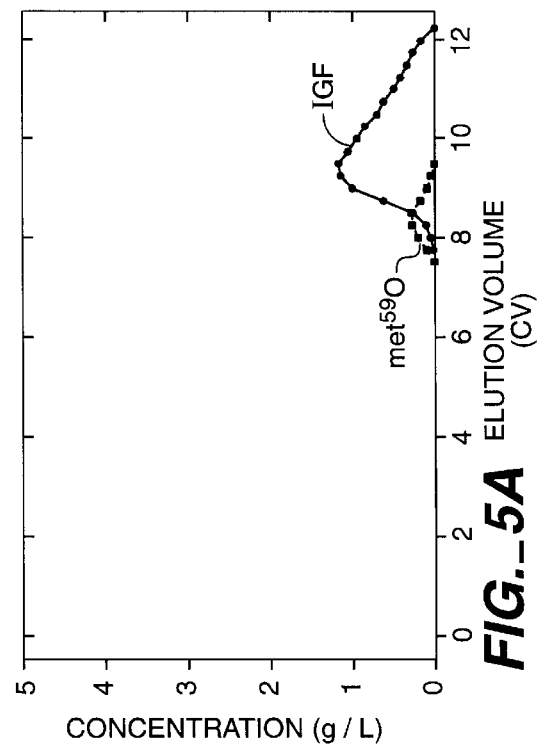
FIG._5C
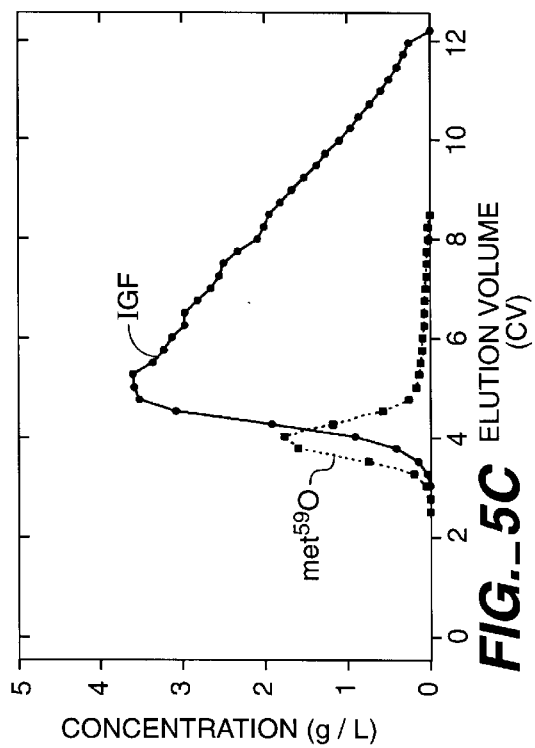
FIG._5D

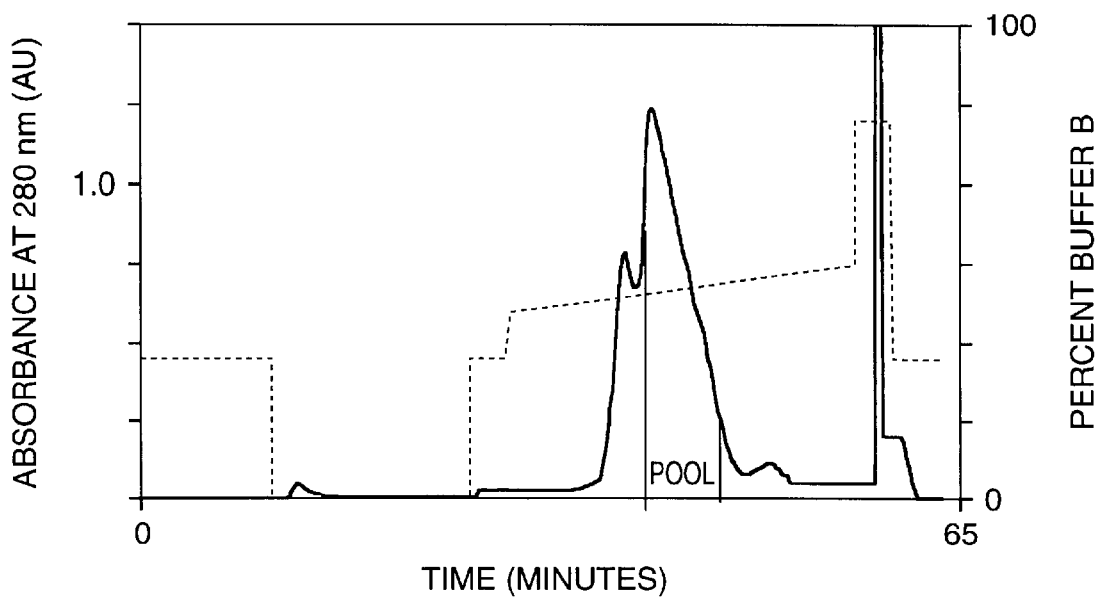
FIG._7A
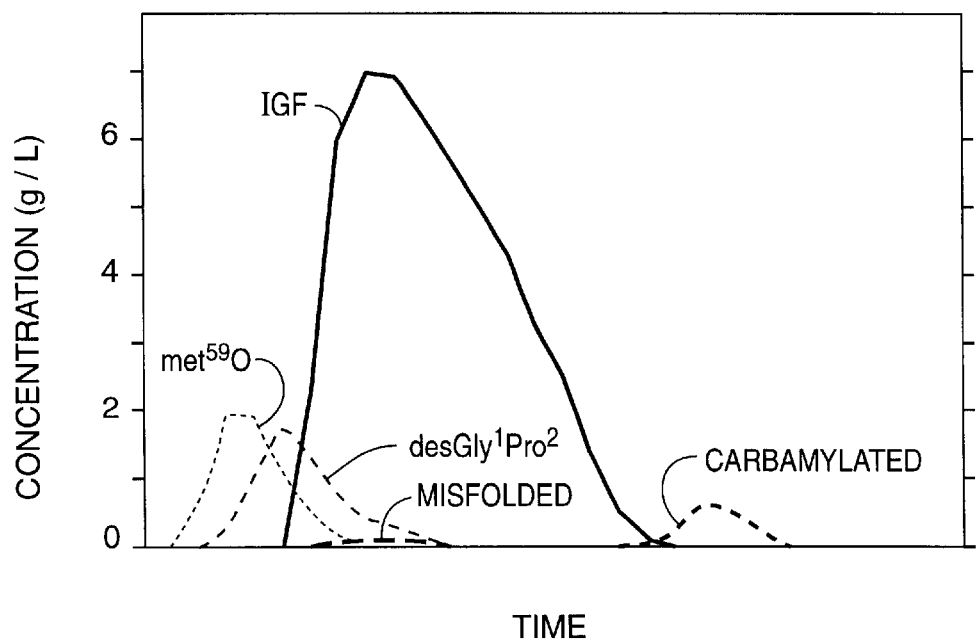
FIG._7B

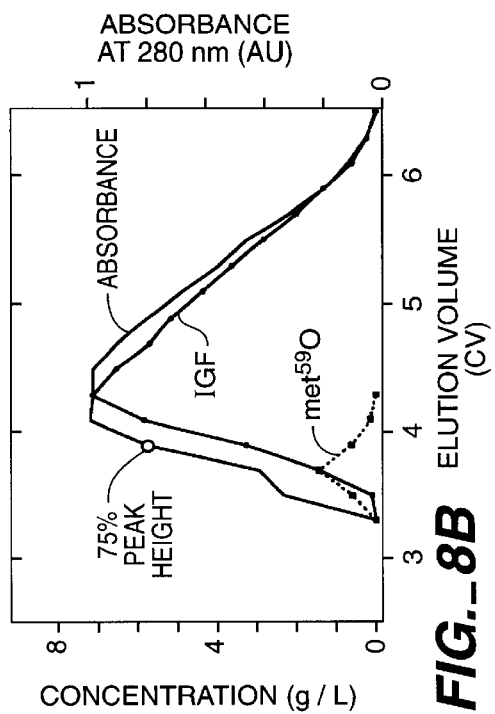
FIG._8A
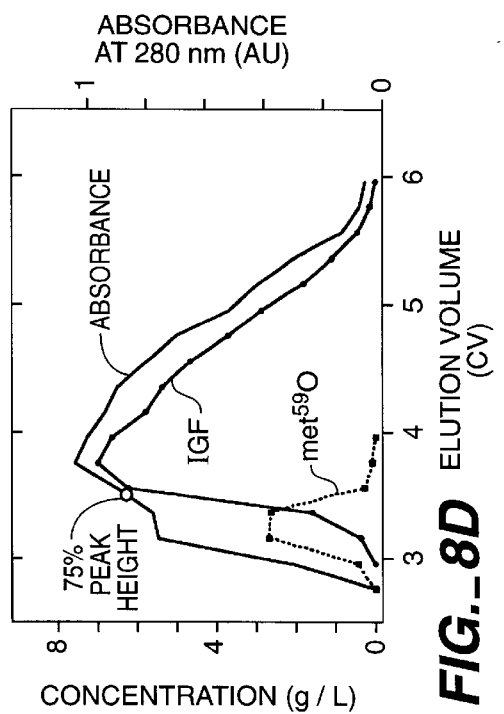
FIG._8B
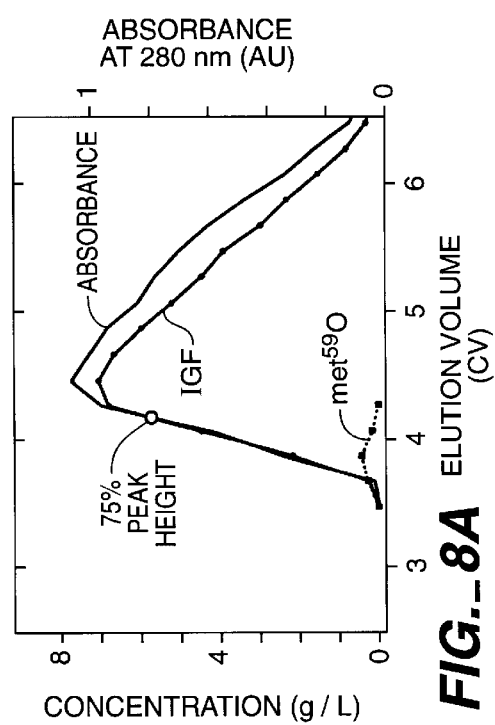
FIG._8C
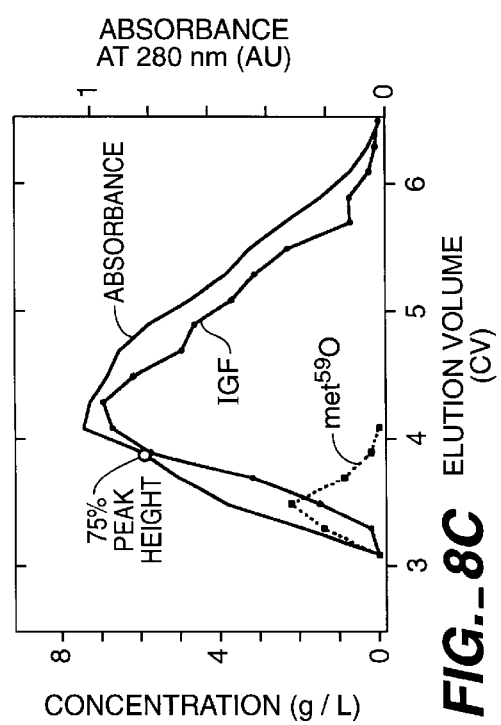
FIG._8D

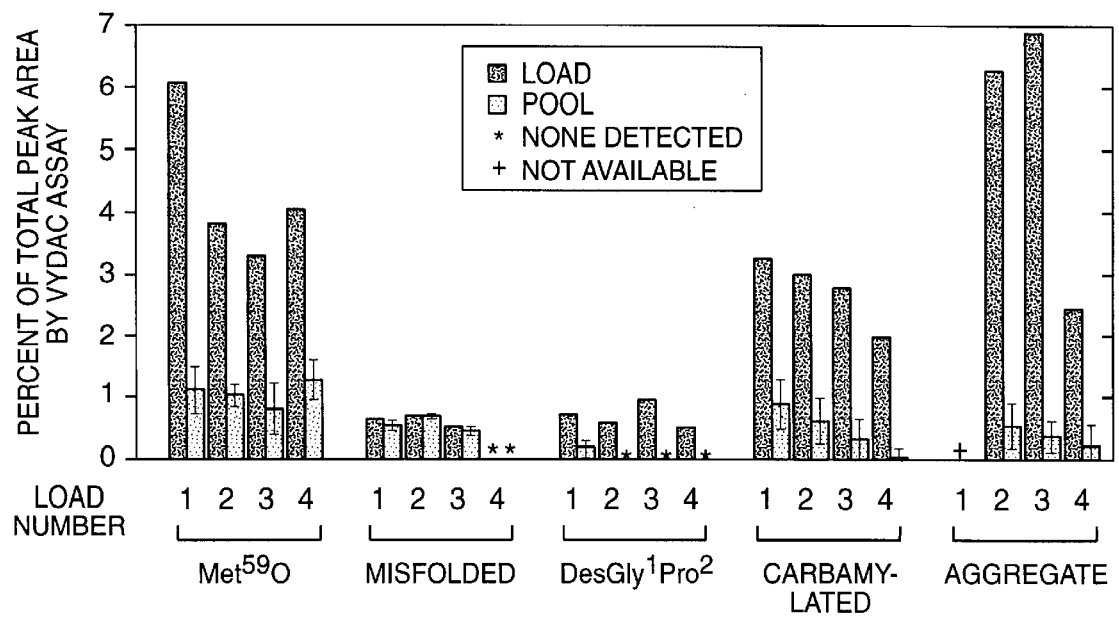
FIG._9
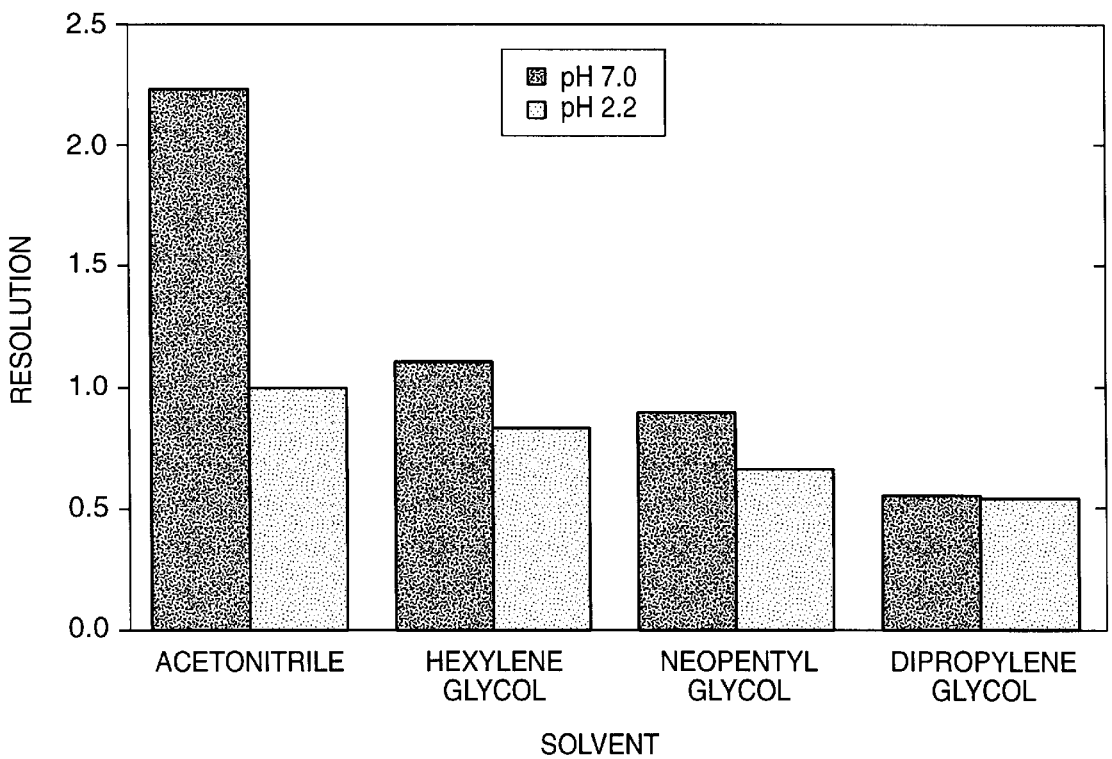
FIG._11

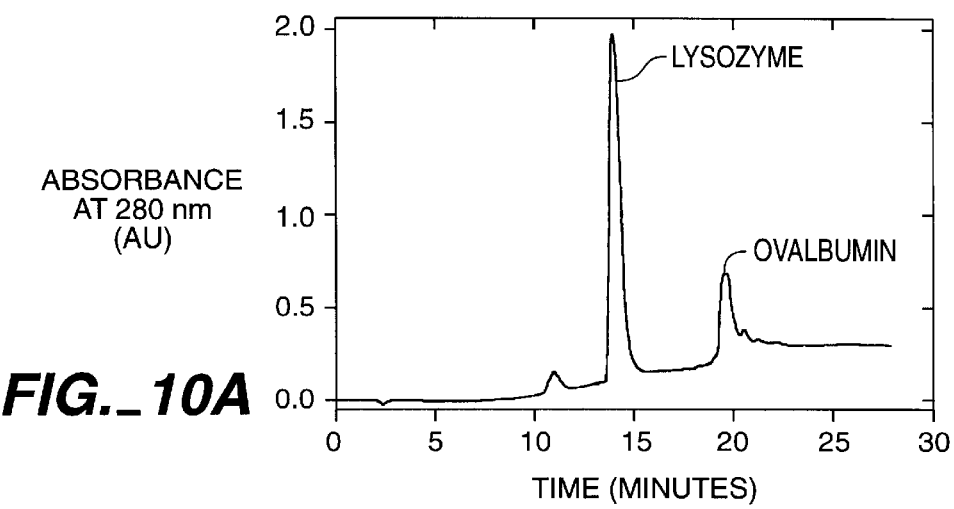
FIG._10A
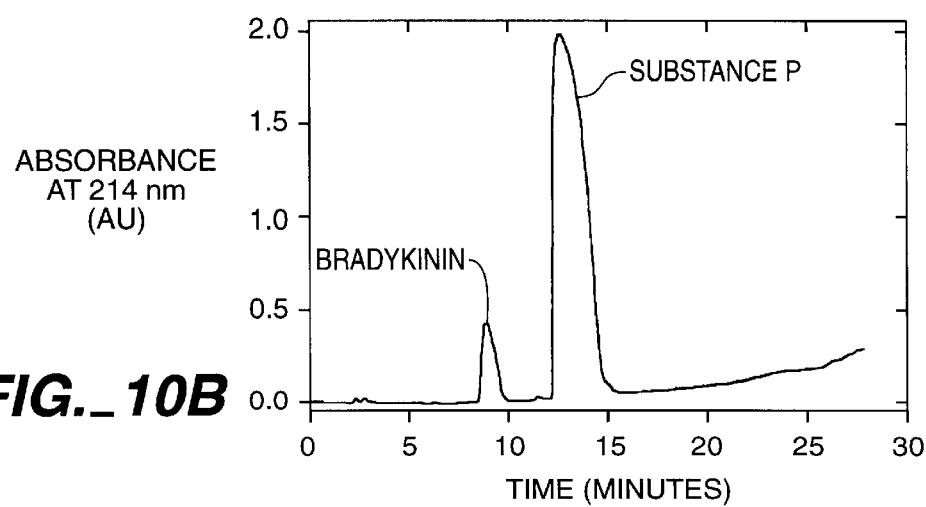
FIG._10B
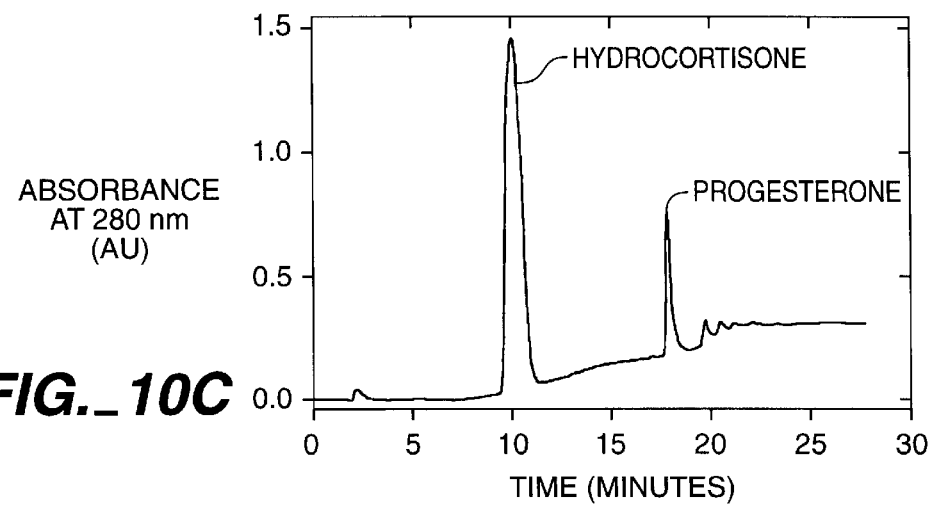
FIG._10C

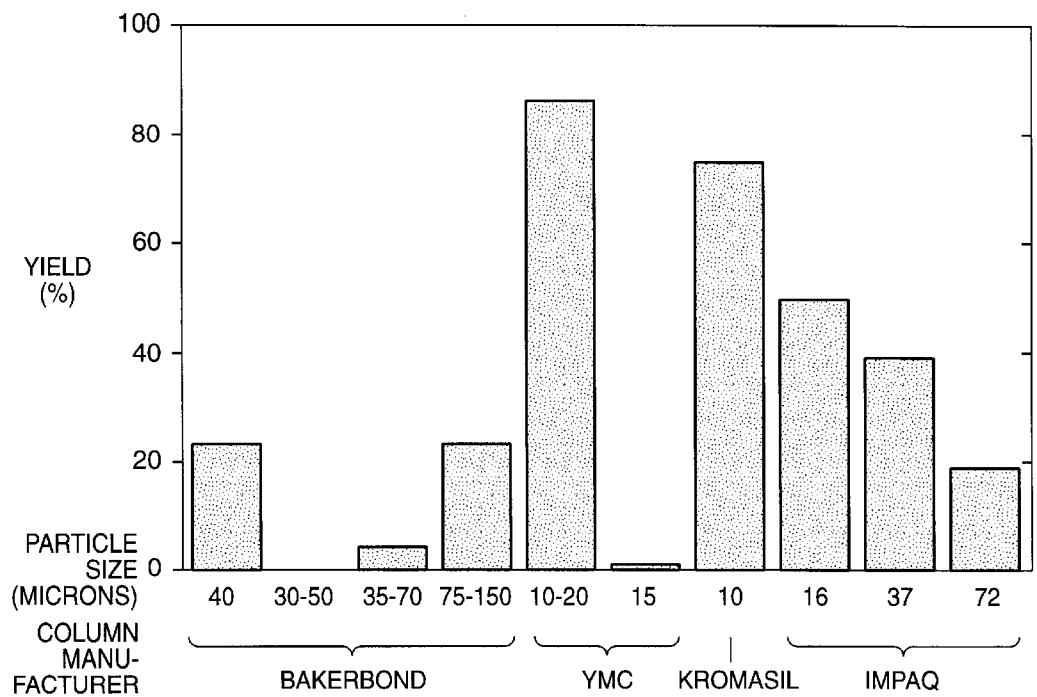
FIG._12
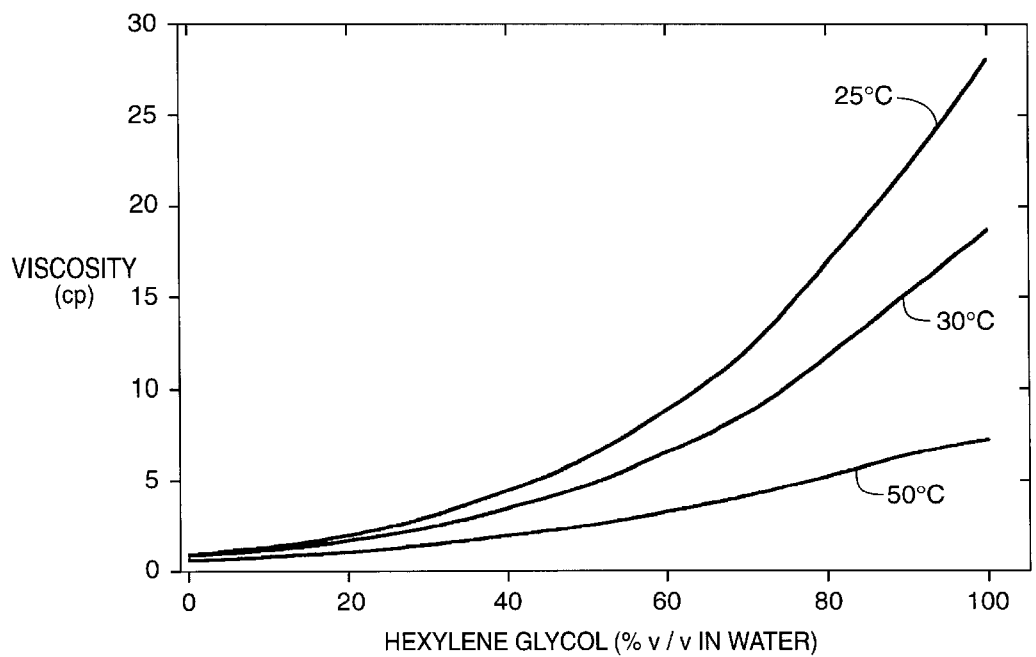
FIG._13

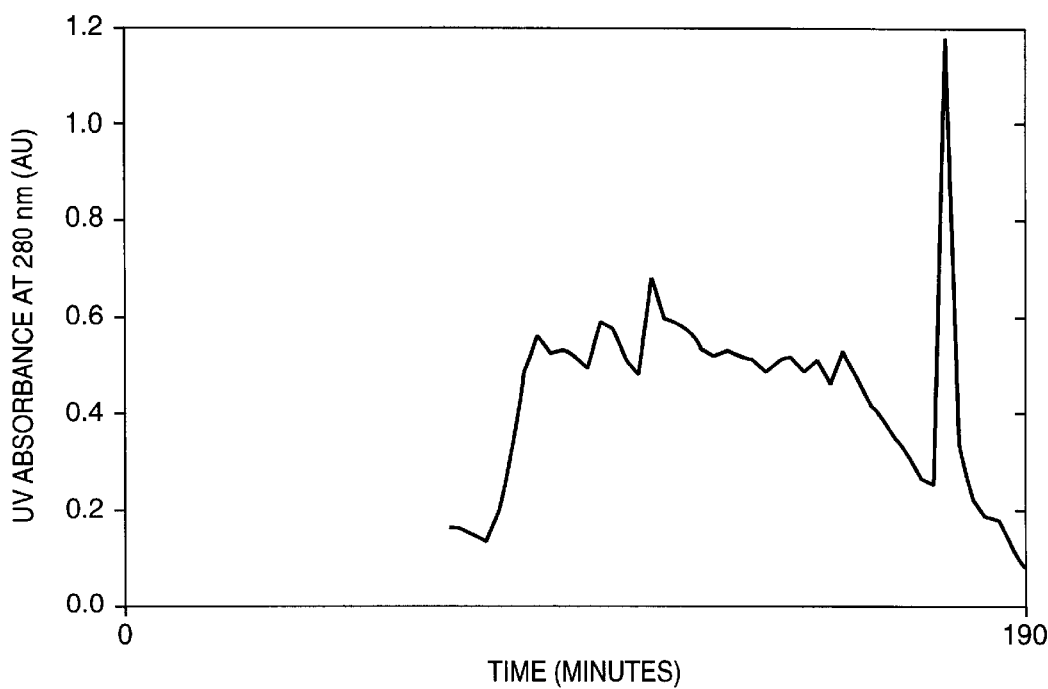
FIG._14A-1
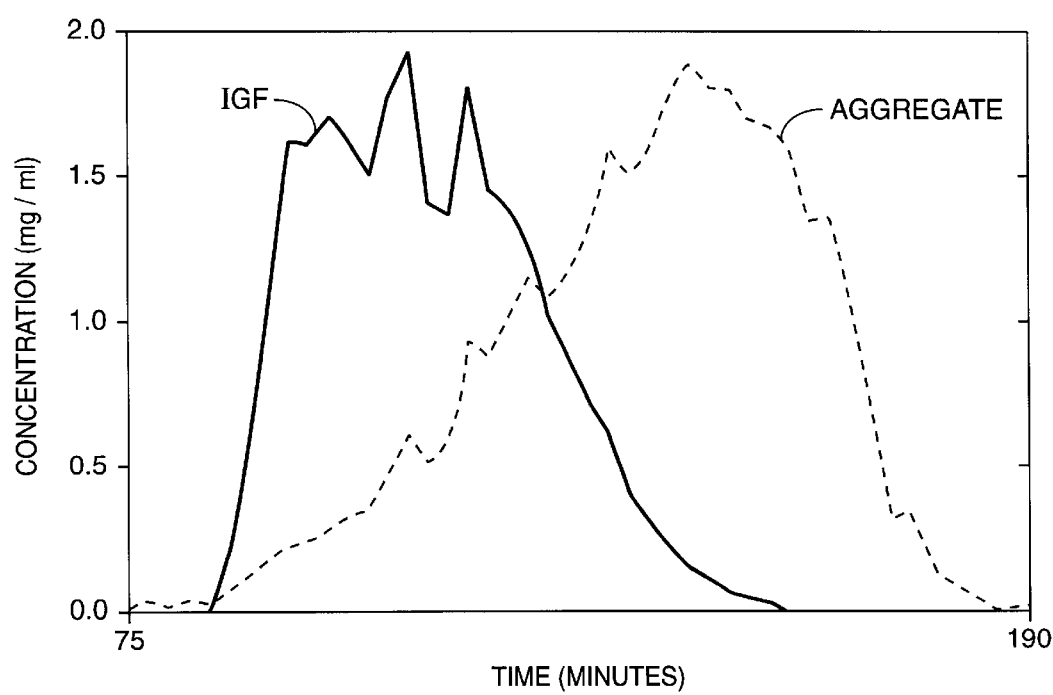
FIG._14A-2

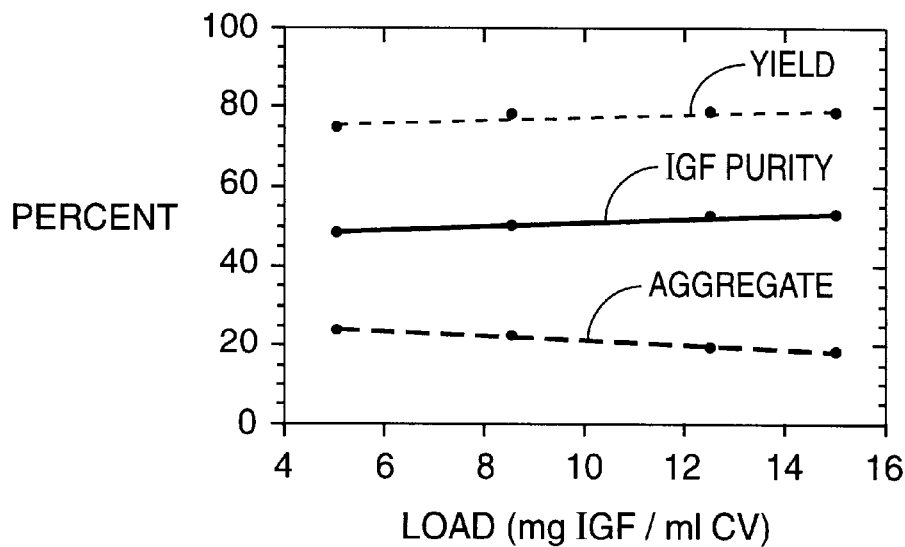
FIG._14B
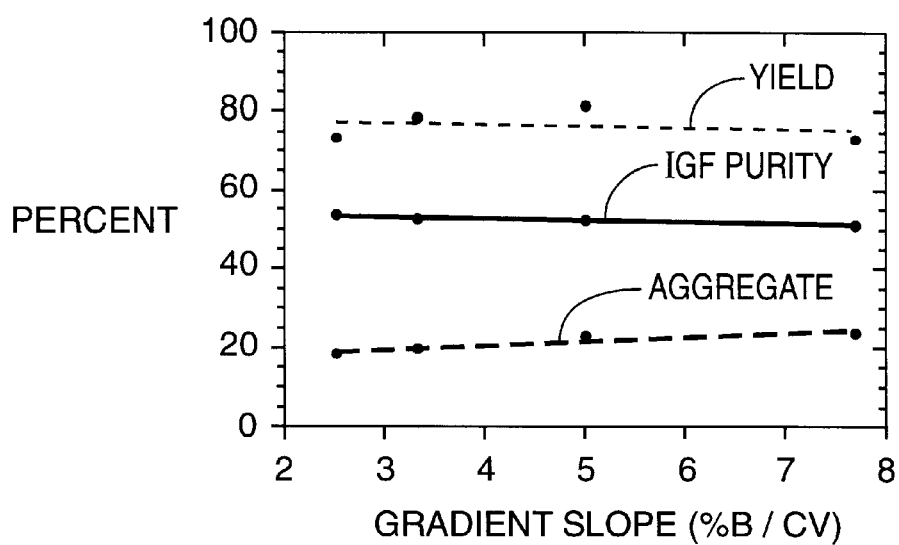
FIG._14C

```
SEQUENCE LISTING

<160> NUMBER OF SEQ ID NOS: 2

<210> SEQ ID NO 1
<211> LENGTH: 9
<212> TYPE: PRT
<213> ORGANISM: Artificial sequence
<220> FEATURE:
<221> NAME/KEY: Artificial sequence
<222> LOCATION: 1-9
<223> OTHER INFORMATION: Sequence is synthesized

<400> SEQUENCE: 1

Arg Pro Pro Gly Phe Ser Pro Phe Arg
 1               5               9

<210> SEQ ID NO 2
<211> LENGTH: 10
<212> TYPE: PRT
<213> ORGANISM: Artificial sequence
<220> FEATURE:
<221> NAME/KEY: Artificial sequence
<222> LOCATION: 1-10
<223> OTHER INFORMATION: Sequence is synthesized

<400> SEQUENCE: 2

Arg Pro Lys Pro Gln Phe Phe Gly Leu Met
 1               5                   10
```

PURIFICATION OF MOLECULES

RELATED APPLICATIONS

This application is a non-provisional application filed under 37 CFR 1.53(b) (1), claiming priority under 35 USC 119(e) to provisional application No. 60/063,119 filed Oct. 24, 1997, the contents of which are incorporated herein by reference.

BACKGROUND OF THE INVENTION

1. Field of the Invention

This invention relates to an improved method for purifying molecules such as peptides, polypeptides, and organic molecules from variants, impurities, and contaminants associated therewith.

2. Description of Related Art

The production of large quantities of relatively pure, biologically active molecules is important economically for the manufacture of human and animal pharmaceutical formulations, enzymes, and other specialty chemicals. For production of many polypeptides and proteins, recombinant DNA techniques have become the method of choice because large quantities of exogenous proteins can be expressed in bacteria and other host cells. The expression of proteins by recombinant DNA techniques for the production of cells or cell parts that function as biocatalysts is also an important application.

Producing recombinant protein involves transfecting host cells with DNA encoding the protein and growing the cells under conditions favoring expression of the recombinant protein. The prokaryote *E. coli* is favored as host because it can be made to produce recombinant proteins in high yields. Numerous U.S. patents on general bacterial expression of DNA encoding proteins exist, including U.S. Pat. No. 4,565,785 on a recombinant DNA molecule comprising a bacterial gene for an extracellular or periplasmic carrier protein and non-bacterial gene; U.S. Pat. No. 4,673,641 on co-production of a foreign polypeptide with an aggregate-forming polypeptide; U.S. Pat. No. 4,738,921 on an expression vector with a trp promoter/operator and trp LE fusion with a polypeptide; U.S. Pat. No. 4,795,706 on expression control sequences to include with a foreign protein; and U.S. Pat. No. 4,710,473 on specific circular DNA plasmids.

Genetically engineered biopharmaceuticals are typically purified from a supernatant containing a variety of diverse host cell contaminants. Reversed-phase high-performance liquid chromatography (RP-HPLC) is commonly used for protein purification because it can efficiently separate closely related protein impurities. Procedures utilizing RP-HPLC have been published for many molecules. McDonald and Bidlingmeyer, "Strategies for Successful Preparative Liquid Chromatography", *Preparative Liquid Chromatography*, Brian A. Bidlingmeyer (New York: Elsevier Science Publishing, 1987), vol. 38, pp. 1–104; Lee et al., Preparative HPLC. 8th Biotechnology Symposium, Pt. 1, 593–610 (1988). Irreversible binding of insulin and proinsulin to C18 stationary phases has recently been reported (Linde and Welinder, *J. Chromatoqr.*, 536: 43 (1991)), with the C4 alkyl chain substitution being preferred to maximize product recovery. Nice et al., *J. Chromatoqr.*, 218: 569 (1981).

Acetonitrile, ethanol, methanol, and isopropanol are often used as eluents for reversed-phase chromatography, and acetonitrile is the most common eluent for this purpose because it produces high-resolution separations. Acetonitrile is used at large scale for purification of recombinant proteins such as insulin. Kroeff et al., *J. Chromatography*, 461: 45–61 (1989). However, acetonitrile and the other common solvents are flammable with all the attendant difficulties, and acetonitrile has a denaturing effect.

Recombinant human insulin-like growth factor-I (rhIGF-I) is a 70 amino acid protein with a pI of 8.4 (Rinderknecht and Humbel, *Proc. Natl. Acad. Sci. USA*, 73: 2365 (1976); Rinderknecht and Humbel, 253: 2769–2776 (1978)) and with a molecular weight of 7649 daltons and three disulfide bonds. Raschdorf et al., *Biomedical and Environmental Mass Spectrometry*, 16: 3–8 (1988).

IGF-I has been purified by RP-HPLC from human plasma (Cornell et al., *Preparative Biochemistry*, 14: 123–138 (1984); Petrides et al., *Endocrinology*, 118: 2034–2038 (1986)) and from recombinant material produced in bacterial fermentation. Olson et al., *J. Chromatography*, A675: 101–112 (1994). See also U.S. Pat. No. 5,446,024 on purifying IGF-I using RP-HPLC, as well as Svoboda et al., *Biochemistry*, 19: 790 (1980); Cornell and Brady, *J. Chromatogr.*, 421: 61 (1987); and Francis et al., *Endocrinology*, 124: 1173 (1989).

RP-HPLC can separate several variant forms of IGF-I, including met$^{59}$O variant (methionine sulfoxide at position 59, identified by Hartmanis and Engstrom, *Techniques in Protein Chemistry*, 327–333 (1989)), desGly$^1$ desGly$^1$Pro$^2$ variant (N-terminal glycine and proline missing), carbamylated variant (chemistry of carbamylation in Qin et al., *J. Biological Chemistry*, 267: 26128–26133 (1992)), and IGF-I aggregates. During HPLC purification of IGF-I, variants must be removed to historical levels, which includes a requirement of less than 2% met$^{59}$O variant. Purity is determined by a VYDAC™ HPLC assay, which is similar to the assay characterized by Canova-Davis et al., *Biochem. J.*, 285: 207–213 (1992). The amounts of each variant can change from batch to batch.

Olson et al., supra, designed parameters for maximum separation of met$^{59}$O variant from IGF-I, with a buffer of 100 mM potassium phosphate at pH 7.0 and elution with acetonitrile. A typical batch size for the HPLC purification step is 12 kg of IGF-I. If the acetonitrile process were scaled directly to the 60-cm diameter column, it would require five cycles to process the batch, for a total processing time of 13 hours. Average recovery yield for the acetonitrile process, calculated as the mass of IGF-I in the purified pool divided by the mass of IGF-I loaded (mass determined by the VYDAC™ assay), is about 80%, and throughput is about 0.3 g hr$^{-1}$ cm$^{-2}$.

There is a need in the art for an efficient reversed-phase liquid chromatography protocol for selectively separating molecules such as peptides, polypeptides, and non-peptidyl compounds from other molecules using a solvent that is less toxic, less expensive, less denaturing, and less flammable than flammable solvents often used as eluents for reversed-phase chromatography, such as acetonitrile, ethanol, methanol, and isopropanol. In particular, there is a need for purifying IGF-I from hydrophobic polypeptides in a fermentation broth, particularly since typically the final process pool contains several variant species of IGF-I that are difficult to separate. This need would be satisfied when the process duplicates as much as possible the yield, purity, throughput, and operating conditions of the liquid chromatography process wherein elution is conducted by a flammable solvent such as acetonitrile.

SUMMARY OF THE INVENTION

This invention provides, in one aspect, a process for purifying a molecule selected from the group consisting of a peptide, a polypeptide, and a biologically active non-peptidyl compound comprising loading a mixture containing the molecule onto a reversed-phase liquid chromatography column and eluting the molecule from the column with a buffer containing hexylene glycol.

While ethanol, methanol, isopropanol, and, in particular, acetonitrile, often provide good protein separations using reversed-phase liquid chromatography, they are flammable solvents (acetonitrile has a flashpoint of about 15° C.), and using them at large scale requires expensive nonflammable-capable equipment and facilities. Further, acetonitrile is somewhat of a denaturant and is toxic to the environment. The method herein was developed to purify molecules by reversed-phase liquid chromatography using the non-flammable eluent hexylene glycol rather than a flammable eluent. Hexylene glycol, with a flashpoint of about 93° C., produced essentially the same yield, purity, and throughput as acetonitrile and with less denaturing effect. Thus, hexylene glycol may be advantageous as an eluent for, e.g., full-length antibodies and some glycosylated proteins, which have a tendency to be denatured when eluted from a reversed-phase liquid chromatography column. Further, hexylene glycol is less toxic to the environment than certain flammable solvents such as acetonitrile and is available in large quantities in USP grade. Also, hexylene glycol was found to be a better eluent for sample displacement than acetonitrile.

Many non-flammable solvents were tested and all except hexylene glycol were found to have one or more of the following problems: insoluble in aqueous solution, too viscous for the column, too weak as an eluent (not eluotropic), too highly absorbing where the molecule of interest absorbs, and/or having endogenous peroxide activity. In contrast, hexylene glycol was soluble in aqueous solution, did not interfere with the spectrum for the molecule of interest, did not have a high viscosity, and was eluotropic.

BRIEF DESCRIPTION OF THE DRAWINGS

FIG. 1 shows a schematic of the 10K/10K IGF-I recovery process used in Example I below, with four stages indicated. During upstream recovery, the IGF-I is solubilized from the cells and two-phase extraction removes cell debris and partially purifies the IGF-I. Folding puts IGF-I into the correct conformation, and clarification by centrifuge removes solids. Acid C4 chromatography removes aggregate, SP-SEPHAROSE™ removes misfolded protein, reversed-phase HPLC removes met$^{59}$O, clipped, carbamylated, and aggregate protein variants; and S-SEPHAROSE™ removes misfolded IGF-I. The IGF-I is then formulated, e.g., using tangential flow filtration (TFF).

FIG. 2 shows the VYDAC™ method for analysis of IGF-I and variants. This high-resolution analysis method can separate several variants from IGF-I.

FIG. 3 shows a typical chromatogram from the HPLC process using elution with acetonitrile. Met$^{59}$O, desgly$^1$, and desGly$^1$Pro$^2$ variants are separated from IGF-I.

FIGS. 4A–4E show a quantitative evaluation of the effect of flow rate, load, gradient slope, temperature, and column length on relative separation efficiency using 1-cm diameter KROMASIL™ (10 μm, 150 angstrom) C4 columns, 100 mM potassium phosphate pH 7.0, and elution with hexylene glycol. Y-axis on all graphs is yield at constant purity calculated by Equation 1 specified below.

FIGS. 5A to 5D show chromatograms from a preparative characterization loading study. Elution volume is volume after gradient start.

FIG. 6A shows the effect of residence time on the formation of misfolded material. FIG. 6B shows clearance of misfolded material on a 6-cm-diameter column with increasing amounts of misfolded material added to the load.

FIG. 7A shows a chromatogram from the HPLC process using hexylene glycol elution on the 6-cm-diameter column and scale-up conditions as described below. Pool lines indicate cut for less than 1% met$^{59}$O variant. Inset (FIG. 7B) is the preparative peak with variants shown as determined by the VYDAC™ assay.

FIGS. 8A–8D show peak cutting. Load material was spiked with purified met$^{59}$O variant. Elution volume is volume after gradient start. Absorbance at 280 nm is shown as a solid line, with 75% peak height indicated by open circles. Fraction analysis by the VYDAC™ assay is shown with solid and dashed lines as indicated.

FIG. 9 shows column cycling using the 6-cm-diameter column and scale-up conditions described in Example I. Pools (light gray) were collected from 75% to 25% peak height based on the height of the first cycle. Four different load materials (dark gray) were used, with 11 cycles of load 1, five cycles of load 2, 19 cycles of load 3, and 32 cycles of load 4. Pool values are averages, and error bars are one standard deviation.

FIG. 10A shows a chromatogram for the separation of two chicken egg proteins, lysozyme and ovalbumin, using a VYDAC™ column and hexylene glycol as the eluent. FIG. 10B shows a chromatogram for the separation of two peptides, bradykinin and Substance P, on a YYDAC™ column using hexylene glycol as the eluent. FIG. 10C shows a chromatogram for the separation of two hormones, hydrocortisone and progesterone, using a VYDAC™ column and hexylene glycol as the eluent.

FIG. 11 shows a solvent screen: analytical scale separation of IGF-I from met$^{59}$O variant using three nonflammable solvents and acetonitrile at pH 7.0 (dark gray) and pH 2.2 (light gray).

FIG. 12 shows yield at constant purity of less than 1% met$^{59}$O variant in percent for column screening. It shows preparative scale separation of IGF-I from met$^{59}$O variant using four different columns of different particle sizes and elution with hexylene glycol.

FIG. 13 shows viscosity of hexylene glycol as a function of its concentration at three different temperatures, 25, 30, and 50 degrees Celsius.

FIG. 14A-1 shows acid C4 chromatography of IGF-I using hexylene glycol. The results of a VYDAC™ assay of resulting fractions are shown in the inset, FIG. 14A-2. FIGS. 14B and 14C show percent yield for this separation as a function of load and gradient slope, respectively.

DESCRIPTION OF THE PREFERRED EMBODIMENTS

A. Definitions

As used herein, "molecule" refers to a peptide, polypeptide, or pharmacologically active non-peptidyl compound. As used herein, "peptide" refers to a molecule with up to about thirty amino acids bonded together, including those with naturally occurring amino acids of the L-isomeric form, those with unnatural amino acids of the D-isomeric form, as well as derivatives or analogues thereof. α-Amino acid analogues include those as defined and described in U.S. Pat. No. 5,493,007. The peptides herein further include those with cyclic and/or exocyclic moieties and those having peptide bonds and amide bonds as defined in the above U.S. Pat. No. 5,493,007.

As used herein, "pharmacologically active non-peptidyl compound" is not a peptide, polypeptide, or protein and exhibits an in vitro or in vivo effect on the tissues or cells of an organism, preferably a mammal, and/or possesses an antigenic function. The compound may mimic the biologic and/or immunologic activities of a native or naturally occurring protein or receptor found in the body. Such effects include biological effects such as, for example, mitogenic, hypertrophic, inotropic, anti-arrhythmic, growth-inhibitory, and neurotrophic activities, as well as the ability to bind with an affinity of at least about $10^6$ L/mole to an antibody capable of binding a known active molecule, such as a protein in its native conformation. Such compounds include synthetic organic or inorganic compounds and generally have a molecular weight of about 200 to 600 daltons. Preferably, the compound is an organic molecule consisting at least of carbon, oxygen, and hydrogen atoms. More preferably, such compound is a prodrug or the moiety of a prodrug that is released from the prodrug as by hydrolysis or enzymatic cleavage. Examples of the prodrugs would include compounds such as esters, amines, imines, amides, and imides that have a group that can be cleaved, such as a hydroxy, amino, imino, amido, imido, or carboxy group.

As used herein, "polypeptide" or "polypeptide of interest" refers generally to peptides and proteins having more than about thirty amino acids. Preferably, the polypeptides are "exogenous," meaning that they are "heterologous," i.e., foreign to the host cell being utilized, such as a human protein produced by a CHO cell, or a yeast polypeptide produced by a mammalian cell, or a human polypeptide produced from a human cell line that is not the native source of the polypeptide.

Examples of polypeptides include molecules such as, e.g., renin, a growth hormone, including human growth hormone; bovine growth hormone; growth hormone releasing factor; parathyroid hormone; thyroid stimulating hormone; lipoproteins; 1-antitrypsin; insulin A-chain; insulin B-chain; proinsulin; thrombopoietin (TPO); follicle stimulating hormone; calcitonin; luteinizing hormone; glucagon; clotting factors such as factor VIIIC, factor IX, tissue factor, and vonwillebrands factor; anti-clotting factors such as Protein C; atrial naturietic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as brain-derived neurotrophic factor (BDNF), neurotrophin-3, -4, -5, or -6 (NT-3, NT-4, NT-5, or NT-6), or a nerve growth factor such as NGF-beta; cardiotrophins (cardiac hypertrophy factor) such as cardiotrophin-1 (CT-1); platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5, as well as other members of the TGF-β superfamily not already mentioned, such as, for example, glial cell derived growth factor (GDNF), neurturin, Lefty, and endometrial bleeding associated factors; Smoothened; insulin-like growth factor-I and -II (IGF-I and IGF-II); des(1–3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; anti-HER-2 antibody; superoxide dismutase; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides.

The preferred exogenous polypeptides of interest are mammalian polypeptides, and most preferred are human polypeptides. Examples of such mammalian polypeptides include TPO, binding proteins, hormones such as growth hormone, t-PA, gp120, anti-HER-2, DNase, growth factors such as IGF-I, IGF-II, and brain IGF-I, relaxin chains, growth hormone releasing factor, insulin chains or proinsulin, urokinase, immunotoxins, neurotrophins, antibodies, and antigens.

The most preferred molecules (peptides, polypeptides, and compounds) herein are growth factors, insulin, TPO, hormones such as growth hormone, hydrocortisone, or progesterone, chicken egg proteins such as lysozyme or ovalbumin, peptides of 5–25 amino acids such as Substance P or bradykinin, antibodies and antibody fragments such as anti-CD11, anti-HER-2, anti-VEGF, anti-CD18, a Fab, or a F(ab')$_2$ of the foregoing, and proteins that bind to hormones or growth factors such as an IGFBP, e.g., IGFBP-3, and still more preferred is an insulin-like growth factor, most preferably IGF-I.

As used herein, "IGF-I" refers to insulin-like growth factor from any species, including bovine, ovine, porcine, equine, avian, and preferably human, in native sequence or in variant form, and from any source, whether natural, synthetic, or recombinantly produced. Preferably, the IGF-I is recombinantly produced. In a preferred method, the IGF-I is cloned and its DNA expressed, e.g., by the process described in EP 128,733 published Dec. 19, 1984.

Preferred for human use is human native-sequence, mature IGF-I, more preferably without a N-terminal methionine, prepared, e.g., by the process described in EP 230,869 published Aug. 5, 1987; EP 128,733 published Dec. 19, 1984; or EP 288,451 published Oct. 26, 1988. More preferably, this native-sequence IGF-I is recombinantly produced and is available from Genentech, Inc., South San Francisco, Calif. for clinical investigations.

The preferred IGF-I variants are those described in U.S. Pat. No. 5,077,276 issued Dec. 31, 1991, in PCT WO 87/01038 published Feb. 26, 1987, and in PCT WO 89/05822 published Jun. 29, 1989, i.e., those wherein at least the glutamic acid residue is absent at position 3 from the N-terminus of the mature molecule or those having a deletion of up to five amino acids at the N-terminus. The most preferred variant has the first three amino acids from the N-terminus deleted (variously designated as brain IGF, tIGF-I, des(1–3)-IGF-I, or des-IGF-I).

As used herein, "buffer" refers to a buffered solution that resists changes in pH by the action of its acid-base conjugate components. The buffer can also be, or it can contain, ion-pair reagents such as trifluoroacetic acid, hydrochloric acid, phosphoric acid, or acetic acid. The buffer for the liquid chromatography aspect of this invention has a preferred pH in the range of about 2.5 to 8. Buffers that will control the pH within this general range include, for example, acetate, citrate, succinate, phosphate, MES, ADA, BIS-TRIS Propane, PIPES, ACES, imidazole, diethylmalonic acid, MOPS, TES, TRIS buffer such as TRIS-HCl, HEPES, HEPPS, TRICINE, glycine amide, BICINE, glycylglycine, and borate buffers.

As used herein, the phrase "phosphate salt" refers to a salt having a cation, preferably from the alkaline earth or alkali metal elements or an ammonium cation, and having a phosphate anion. Examples of such salts include sodium phosphate, calcium phosphate, ammonium phosphate, magnesium phosphate, and potassium phosphate. The most preferred salts herein are sodium and potassium phosphate.

As used herein, "non-flammable" solvents or glycols refers to any type of solvent or glycol, for example, those with 1 to 10 carbon atoms, that has a flashpoint of generally about 60–100° C. This would preferably exclude propylene glycol, ethylene glycol, polypropylene glycol, and polyethylene glycol. Examples of non-flammable solvents include hexylene glycol, dipropylene glycol, butylene glycol, pentylene glycol, isobutylene glycol, isopentylene glycol, neopentyl glycol, octylene glycol, diethylene glycol, 3-hydroxyl propionitrile, etc. The most preferred for all separations is hexylene glycol, and hexylene glycol is utilized for the reverse-phase liquid chromatography step claimed herein.

B. Modes for Carrying Out the Invention

The first step of the process herein involves purifying molecules from mixtures containing them by loading the mixtures on a reversed-phase liquid chromatography column. The column may be low-pressure (such as an acid C4 column as noted above) or high-pressure (HPLC), the latter of which is packed with a medium having a particle diameter less than about 20 $\mu$m. Preferably, the column is packed with a medium having a particle diameter of about 5–40 $\mu$m, more preferably about 10–40 $\mu$m, and most preferably about 10–15 $\mu$m. Hence, the column is preferably an HPLC column, especially for purification of peptides that require it. Preferably, the column has a pore size of about 100–4000 angstroms, more preferably about 150–300 angstroms. The column length is preferably 10–50 cm, more preferably about 25–35 cm.

The medium of the column may be any suitable material, including polymeric-based media, silica-based media, or methacrylate media. Preferably, the medium is a silica, and more preferably a silica with a C4–C18 alkyl group, such as KROMASIL™ C4, C6, C12, or C18.

The column may be an analytical or preparative column. The amount of molecule loaded onto the column is generally about 0.01 to 40 g molecule/liter bed volume, preferably about 0.02 to 30 g molecule/liter bed volume, more preferably about 1 to 25 g molecule/liter bed volume, and most preferably about 3 to 25 g molecule/liter bed volume. Preferably, the column is a preparative column, meaning preparative scale and/or preparative load. The preparative-scale column has a diameter of at least about 1 cm, preferably, at least about 6 cm, up to and including about 15 cm, 60 cm, or higher. The preparative-load column has a load of molecule of at least about 0.1 g molecule/liter bed volume, preferably at least about 1 g molecule/liter.

The loading solvent may be any solvent but is preferably a non-flammable solvent such as hexylene glycol, neopentyl glycol, dipropylene glycol, or polypropylene glycol, especially when large-scale purifications are being performed. More preferably, the solvent is at a concentration of about 5 to 20% (v/v), more preferably 10 to 20% (v/v) of the solution, depending, e.g., on the type of solvent. If the concentration is too high, the molecule flows through the column.

The flow rate is generally about 50–400 cm/hour, or 4–20 column volumes (CV)/hour, depending on whether the chromatography is acidic or neutral. The gradient slope is preferably about 0.1–0.7% (w/w) hexylene glycol/CV.

In the second step of the process herein, the molecule is eluted from the column with a buffer containing hexylene glycol. Preferably, the buffer is at a pH of about 2.5 to 8, where it is about 2.5 to 5 to provide acidic chromatography, or is about 6 to 7.5 to provide more neutral chromatography. Preferably, the buffer is a phosphate, acetate, and/or citrate buffer, although other buffers may be employed, provided that they maintain the pH in the desired range for the purification. If the buffer is other than phosphate buffer, a different salt from the salts forming the buffer, preferably sodium chloride or potassium chloride, is added to the buffer in an amount of from about 10 mM up to the solubility limit of the salt.

If the buffer is a phosphate buffer, preferably the phosphate is at a concentration of about 10 mM to the solubility limit of the salt. More preferably, the concentration of the phosphate salt in the preferred buffer is about 10–200 mM, more preferably about 15–150 mM. Most preferably, the buffer is about 100 mM sodium or potassium phosphate, pH adjusted to about 6–7.5.

The amount of hexylene glycol employed for elution will vary depending on, for example, the type of molecule being purified and the type of column utilized. Thus, for example, to purify IGF-I or structurally similar molecules such as IGF-II, brain IGF, and other IGF family members and analogs using RP-HPLC, the concentration of hexylene glycol to be used typically is about 10–15% (v/v). For low-pressure liquid chromatography separation (for example, acid C4 separation) of such molecules, the concentration is typically about 10–20% (v/v). In general, however, the concentration of the molecule ranges from about 10 to 40% (v/v), more preferably about 10 to 30% (v/v).

The temperature of the elution is generally at about 20–80° C., although higher or lower temperatures may be employed. Preferably, the temperature is maintained at about 20–40° C. for acidic C4 chromatography, and at about 30–80° C. for neutral chromatography.

The preferred conditions for IGF-I elution from its variants are the use of a 6-cm to 60-cm diameter RP-HPLC column with 10–15 micron silica C4 medium and phosphate buffer, with a load of 1–25 g IGF-I/liter CV and using 10–15% (v/v) hexylene glycol. The most preferred conditions for IGF-I elution from its variants are a 60-cm diameter RP-HPLC column with 10 micron KROMASIL™-brand silica C4 medium and 100 mM potassium phosphate buffer at pH 6–7.5, with a load at 3–25 g IGF-I/liter CV and using 10–15% (v/v) hexylene glycol.

The process above can be used to purify polypeptides from their variants, usually after the polypeptide has already been purified from most other impurities. Hence, this step is typically the final one before desalting or diafiltration prior to therapeutic formulation. While the polypeptide in the mixture of variants may be produced from any source, preferably it is made recombinantly. The related variants that may be in the mixture include not only variants residual from a fermentation, but also variants produced if the polypeptide is degraded on storage.

If the polypeptide is prepared recombinantly, suitable host cells for expressing the DNA encoding the polypeptide are prokaryote, yeast, or higher eukaryotic cells. Suitable prokaryotes for this purpose include bacteria such as archaebacteria and eubacteria. Preferred bacteria are eubacteria, such as Gram-negative or Gram-positive organisms, for example, Enterobacteriaceae such as Escherichia, e.g., *E. coli*, Enterobacter, Erwinia, Klebsiella, Proteus, Salmonella, e.g., *Salmonella typhimurium*, Serratia, e.g., *Serratia*

*marcescans*, and Shigella; Bacilli such as *B. subtilis* and *B. licheniformis* (e.g., *B. licheniformis* 41P disclosed in DD 266,710 published Apr. 12, 1989); Pseudomonas such as *P. aeruginosa*; Streptomyces; Azotobacter; Rhizobia; Vitreoscilla; and Paracoccus. Suitable *E. coli* hosts include *E. coli* W3110 (ATCC 27,325), *E. coli* 294 (ATCC 31,446), *E. coli* B, and *E. coli* X1776 (ATCC 31,537). These examples are illustrative rather than limiting.

Mutant cells of any of the above-mentioned bacteria may also be employed. It is, of course, necessary to select the appropriate bacteria taking into consideration replicability of the replicon in the cells of a bacterium. For example, *E. coli*, Serratia, or Salmonella species can be suitably used as the host when well known plasmids such as pBR322, pBR325, pACYA177, or pKN410 are used to supply the replicon.

*E. coli* strain W3110 is a preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tona ptr3 phoA E15 (argF-lac)169 degP ompT kan$^r$; *E. coli* W3110 strain 37D6, which has the complete genotype tonA ptr3 phoA E15 (argF-lac)169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued Aug. 7, 1990.

In addition to prokaryotes, eukaryotic microbes such as filamentous fungi or yeast are suitable expression hosts for polypeptide-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe* (Beach and Nurse, *Nature*, 290: 140 (1981); EP 139,383 published May 2, 1985); Kluyveromyces hosts (U.S. Pat. No. 4,943,529; Fleer et al., *Bio/Technology*, 9: 968–975 (1991)) such as, e.g., *K. lactis* (MW98-8C, CBS683, CBS4574; Louvencourt et al., *J. Bacteriol.*, 737 (1983)), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology*, 8: 135 (1990)), *K. thermotolerans*, and *K. marxianus*; *yarrowia* (EP 402,226); *Pichia pastoris* (EP 183,070; Sreekrishna et al., *J. Basic Microbiol.*, 28: 265–278 (1988)); Candida; *Trichoderma reesia* (EP 244,234); *Neurospora crassa* (Case et al., *Proc. Natl. Acad. Sci. USA*, 76: 5259–5263 (1979)); Schwanniomyces such as *Schwanniomyces occidentalis* (EP 394,538 published Oct. 31, 1990); and filamentous fungi such as, e.g., Neurospora, Penicillium, Tolypocladium (WO 91/00357 published Jan. 10, 1991), and Aspergillus hosts such as *A. nidulans* (Ballance et al., *Biochem. Biophys. Res. Commun.*, 112: 284–289 (1983); Tilburn et al., *Gene*, 26: 205–221 (1983); Yelton et al., *Proc. Natl. Acad. Sci. USA*, 81: 1470–1474 (1984)) and A. niger (Kelly and Hynes, *EMBO J.*, 4: 475–479 (1985)).

Suitable host cells appropriate for the expression of the DNA encoding the polypeptide may also be derived from multicellular organisms. Such host cells are capable of complex processing and glycosylation activities. In principle, any higher eukaryotic cell culture is suitable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. See, e.g., Luckow et al., *Bio/Technology*, 6: 47–55 (1988); Miller et al., in *Genetic Engineering*, Setlow, J. K. et al., eds., Vol. 8 (Plenum Publishing, 1986), pp. 277–279; and Maeda et al., *Nature*, 315: 592–594 (1985). A variety of viral strains for transfection are publicly available, e.g., the L-1 variant of *Autographa californica* NPV and the Bm-5 strain of *Bombyx mori* NPV, and such viruses may be used herein, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the DNA encoding the polypeptide. During incubation of the plant cell culture with *A. tumefaciens*, the DNA encoding the polypeptide is transferred to the plant cell host such that it is transfected, and will, under appropriate conditions, express the DNA encoding the polypeptide. In addition, regulatory and signal sequences compatible with plant cells are available, such as the nopaline synthase promoter and polyadenylation signal sequences. Depicker et al., *J. Mol. Appl. Gen.*, 1: 561 (1982). In addition, DNA segments isolated from the upstream region of the T-DNA 780 gene are capable of activating or increasing transcription levels of plant-expressible genes in recombinant DNA-containing plant tissue. EP 321,196 published Jun. 21, 1989.

Examples of useful mammalian host cell lines are the monkey kidney CV1 line transformed by SV40 (COS-7, ATCC CRL 1651); human embryonic kidney line (293 or 293 cells subcloned for growth in suspension culture, Graham et al., *J. Gen Virol.*, 36: 59 (1977)); baby hamster kidney cells (BHK, ATCC CCL 10); Chinese hamster ovary cells/-DHFR (CHO, Urlaub and Chasin, *Proc. Natl. Acad. Sci. USA*, 77: 4216 (1980)); mouse sertoli cells (TM4, Mather, *Biol. Reprod.*, 23: 243–251 (1980)); monkey kidney cells (CV1, ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.*, 383: 44–68 (1982)); MRC 5 cells; FS4 cells; and a human hepatoma line (Hep G2).

Host cells are transfected and preferably transformed with the above-described expression or cloning vectors and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., *Molecular Cloning: A Laboratory Manual* (New York: Cold Spring Harbor Laboratory Press, 1989), or electroporation is generally used for prokaryotes or other cells that contain substantial cell-wall barriers. Infection with Agrobacterium tumefaciens is used for transformation of certain plant cells, as described by Shaw et al., *Gene*, 23: 315 (1983) and WO 89/05859 published Jun. 29, 1989. In addition, plants may be transformed using ultrasound treatment as described in WO 91/00358 published Jan. 10, 1991.

For mammalian cells without such cell walls, the calcium phosphate precipitation method of Graham and van der Eb, *Virology*, 52: 456–457 (1978) is preferred. General aspects of mammalian cell host system transformations have been described by Axel in U.S. Pat. No. 4,399,216 issued Aug. 16, 1983. Transformations into yeast are typically carried out according to the methods of Van Solingen et al., *J. Bact.*, 130: 946 (1977) and Hsiao et al., *Proc. Natl. Acad. Sci. (USA)*, 76: 3829 (1979). However, other methods for introducing DNA into cells, such as by nuclear microinjection, electroporation, bacterial protoplast fusion with intact cells, or polycations, e.g., polybrene, polyornithine, etc., may also be used. For various techniques for transforming mammalian cells, see Keown et al., *Methods in Enzymology* (1990) Vol. 185, pp. 527–537; and Mansour et al., *Nature*, 336: 348–352 (1988).

If prokaryotic cells are used to produce the polypeptide, they are cultured in suitable media in which the promoter can be constitutively or artificially induced as described generally, e.g., in Sambrook et al., *Molecular Cloning: A Laboratory Manual* (Cold Spring Harbor Laboratory Press, NY 1989). Examples of suitable media are given below in the example section.

Any necessary supplements besides carbon, nitrogen, and inorganic phosphate sources may also be included at appropriate concentrations introduced alone or as a mixture with another supplement or medium such as a complex nitrogen source. The pH of the medium may be any pH from about 5 to 9, depending mainly on the host organism.

If mammalian host cells are used to produce the polypeptide, they may be cultured in a variety of media. Commercially available media such as Ham's F10 (Sigma), Minimal Essential Medium (MEM, Sigma), RPMI-1640 (Sigma), and Dulbecco's Modified Eagle's Medium (DMEM, Sigma) are suitable for culturing the host cells. In addition, any of the media described in Ham and Wallace, *Meth. Enz.*, 58: 44 (1979); Barnes and Sato, *Anal. Biochem.*, 102: 255 (1980); U.S. Pat. Nos. 4,767,704; 4,657,866; 4,927,762; 5,122,469; or 4,560,655; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In general, principles, protocols, and practical techniques for maximizing the productivity of in vi tro mammalian cell cultures can be found in *Mammalian Cell Biotechnology: A Practical Approach*, M. Butler, ed. (IRL Press at Oxford University Press, Oxford, 1991).

The above process can be employed whether the polypeptide is produced intracellularly, produced in the periplasmic space, or directly secreted into the medium. In one example of the embodiment where the polypeptide is directly secreted into the medium, at the end of the fermentation the cells are heat-killed and inactivated and the medium is separated from the cellular debris by centrifugation. The clarified fermentation broth is then used for purification on silica.

For the silica chromatography, typically the broth is passed through underivatized silica particles such that the polypeptide adheres to the silica particles; the silica particles are washed to remove contaminants; and the polypeptide is eluted from the silica particles with a buffer comprising an alcoholic or polar aprotic solvent and an alkaline earth, an alkali metal, or an inorganic ammonium salt. Preferably, the buffer is at pH of about 5–8 comprising about 5–40% (v/v) of an alcoholic or polar aprotic solvent and about 0.2 to 3 M of an alkaline earth, an alkali metal, or an inorganic ammonium salt. For other details, see U.S. Pat. No. 5,451,660.

In one example of the embodiment where the polypeptide is produced in the periplasmic space, the culture medium or lysate is centrifuged to remove particulate cell debris. The membrane and soluble protein fractions may then be separated if necessary. The polypeptide may then be purified from the soluble protein fraction and from the membrane fraction of the culture lysate, depending on whether the polypeptide is membrane bound, is soluble, or is present in an aggregated form. The polypeptide thereafter is solubilized and then subsequently refolded using an appropriate buffer. The details for this method of isolation from the periplasm to produce refolded protein are described below.

Insoluble, non-native polypeptide is isolated from the prokaryotic host cells in a suitable isolation buffer by any appropriate technique, e.g., one involving exposing the cells to a buffer of suitable ionic strength to solubilize most host proteins, but in which aggregated polypeptide is substantially insoluble, and disrupting the cells so as to release the inclusion bodies and make them available for recovery by, for example, centrifugation. This technique is well known, and is described, for example, in U.S. Pat. No. 4,511,503.

Briefly, the cells are suspended in the buffer (typically at pH about 5 to 9, preferably about 6 to 8, using an ionic strength of about 0.01 to 2 M, preferably 0.1 to 0.2 M). Any suitable salt, including sodium chloride, is useful to maintain a sufficient ionic strength value. The cells, while suspended in this buffer, are then disrupted by lysis using techniques commonly employed such as, for example, mechanical methods, e.g., a Manton-Gaulin press, a French press, or a sonic oscillator, or by chemical or enzymatic methods.

Examples of chemical or enzymatic methods of cell disruption include spheroplasting, which entails the use of lysozyme to lyse the bacterial wall (Neu et al., *Biochem. Biophys. Res. Comm.*, 17: 215 (1964)), and osmotic shock, which involves treatment of viable cells with a solution of high tonicity and with a cold-water wash of low tonicity to release the polypeptides. Neu et al., *J. Biol. Chem.*, 240: 3685–3692 (1965). A third method, described in U.S. Pat. No. 4,680,262, involves contacting the transformed bacterial cells with an effective amount of a lower alkanol having 2 to 4 carbon atoms for a time and at a temperature sufficient to kill and lyse the cells.

After the cells are disrupted, the suspension is typically centrifuged to pellet the inclusion bodies. In one embodiment, this step is carried out at about 500 to 15,000× g, preferably about 12,000×g, in a standard centrifuge for a sufficient time that depends on volume and centrifuge design, usually about 10 minutes to 0.5 hours. The resulting pellet contains substantially all of the insoluble polypeptide fraction, but if the cell disruption process is not complete, it may also contain intact cells or broken cell fragments. Completeness of cell disruption can be assayed by resuspending the pellet in a small amount of the same buffer solution and examining the suspension with a phase-contrast microscope. The presence of broken cell fragments or whole cells indicates that additional disruption is necessary to remove the fragments or cells and the associated non-refractile polypeptides. After such further disruption, if required, the suspension is again centrifuged and the pellet recovered, resuspended, and analyzed. The process is repeated until visual examination reveals the absence of broken cell fragments in the pelleted material or until further treatment fails to reduce the size of the resulting pellet.

In an alternative embodiment, the polypeptide is isolated from the periplasmic space by solubilization in a suitable buffer. This procedure can be in-situ solubilization involving direct addition of reagents to the fermentation vessel after the polypeptide has been produced recombinantly, thereby avoiding extra steps of harvesting, homogenization, and centrifugation to obtain the polypeptide. The remaining particulates can be removed by centrifugation or filtration, or combinations thereof. Alternatively, and more preferably, one may use a multiple-phase isolation/extraction system for purifying polypeptide from the remaining particulates, as described in U.S. Pat. No. 5,407,810.

Once obtained from the liquid phase of the multiple-phase system, or at a later stage of purification, the polypeptide is suitably refolded into an active conformation as described, for example, in U.S. Pat. No. 5,663,304. The degree of refolding that occurs may be suitably determined by the RIA titer of the polypeptide or by HPLC analysis using e.g., a VYDAC™ or BAKER™ C-18 column, with increasing RIA titer or correctly folded polypeptide peak size directly correlating with increasing amounts of correctly folded, biologically active polypeptide conformer present in the buffer. The incubation is carried out to maximize the yield of correctly folded polypeptide conformer and the ratio of correctly folded polypeptide conformer to misfolded polypeptide conformer recovered, as determined by RIA or HPLC, and to minimize the yield of multimeric, associated polypeptide as determined by mass balance.

After the polypeptide is refolded, the following procedures, individually or in combination, are exemplary of suitable purification procedures for obtaining greater purity: fractionation on immunoaffinity or ion-exchange columns; ethanol precipitation; reversed-phase HPLC; hydrophobic interaction chromatography; chromatography on silica; chromatography on an ion-exchange resin such as S-SEPHAROSE™ and DEAE; chromatofocusing; SDS-PAGE; ammonium sulfate precipitation; and gel filtration using, for example, SEPHADEX™ G-75.

In a preferred embodiment, the folded pool, clarified by centrifugation, is pH adjusted to about 3–8, preferably about 3–5, more preferably about 3.5, and loaded directly onto a low-pressure reversed-phase column. The loading buffer preferably comprises about 5–40% (v/v), preferably 10–30%, of an alcoholic or polar aprotic solvent and about 0.2 to 3 M, preferably about 0.5 to 2 M, of an alkaline earth or alkali metal salt. Preferably, the solvent is methanol, ethanol, iso-propanol, n-propanol, t-butanol, dimethylsulfoxide, dimethylformamide, N-methylpyrrolidone, tetrahydrofuran, dioxane, or acetonitrile, or a non-flammable solvent or glycol, and the alkaline earth or alkali metal salt is a sodium or potassium salt. More preferably, the solvent is ethanol and the sodium or potassium salt is a chloride or sulfate salt. The loading buffer may also contain a chaotropic agent such as urea or guanidine hydrochloride, preferably urea, at a concentration of about 1 to 5 M.

The column is then washed with a buffer at pH preferably about 3 to remove impurities, and the polypeptide is eluted with a gradient or increasing percentage of about 0 to 40% (v/v) of the solvent containing about 0.02 to 0.1 M of the salt in a buffer at preferably about pH 3. The pH 3 buffer is preferably acetic acid. Preferably, the elution is achieved using a buffer of 50 mM acetic acid, 50 mM sodium chloride, and a linear gradient from 28 to 32% (v/v) ethanol.

This pool from either the silica column or the low-pressure reversed-phase column is then loaded on a cation-exchange column such as a S-SEPHAROSE™ column. After washing, which can be done with Tris buffer, the column is eluted with a buffered salt at a pH of about 5–7, such as a citrate buffer at pH 6.

Starting with a partially purified process pool, such as those mentioned above, the mixture of molecule (such as polypeptide) and its impurities (such as variants) is loaded onto a reversed-phase liquid chromatography column and the process as described above is carried out.

After the molecule is eluted from the column, it is suitably formulated into a pharmaceutical composition as follows. The eluate is pH adjusted to a range of about 3–5, preferably 3.5, loaded on a cation-exchange column such as S-SEPHAROSE™ or SP-SEPHAROSE™, washed, and eluted with a buffered salt at about pH 5–6, such as citrate. After this step the molecule is formulated with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to molecules. This formulation step is achieved by desalting or diafiltering using standard technology, such as tangential flow filtration, as set forth, for example, in U.S. Pat. Nos. 5,256,294 and 5,490,937.

Generally, the formulations are prepared by contacting the molecule uniformly and intimately with liquid carriers or finely divided solid carriers or both, to form a pharmaceutical composition. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counter-ions such as sodium; and/or nonionic surfactants such as polysorbates, poloxamers, or PEG.

The molecule is typically formulated in such vehicles at a concentration of about 0.1 mg/mL to 100 mg/mL, preferably 1 to 10 mg/mL, at a pH of about 3 to 8, depending on at what pH the molecule is most stable. It will be understood that use of certain of the foregoing excipients, carriers, or stabilizers will result in the formation of salts of the molecule. If this formulation is to be stored, it is preferably formulated in a buffer at a pH of about 5–7, such as citrate or acetate, with a surfactant that increases the solubility of the molecule at this pH, such as 0.1% polysorbate 20 or POLOXAMER™ 188.

The molecule to be used for therapeutic administration must be sterile. Sterility is readily accomplished by filtration through sterile filtration membranes (e.g., 0.2 micron membranes). Therapeutic molecule compositions generally are placed into a container having a sterile access port, for example, an intravenous solution bag or vial having a stopper pierceable by a hypodermic injection needle.

The molecule ordinarily will be stored in unit or multi-dose containers, for example, sealed ampoules or vials, as an aqueous solution, or as a lyophilized solid formulation for reconstitution. As an example of a lyophilized formulation, 10-mL vials are filled with 5 mL of sterile-filtered 1% (w/v) aqueous molecule solution, and the resulting mixture is lyophilized. The infusion solution is prepared by reconstituting the lyophilized molecule using bacteriostatic Water-for-Injection.

The invention will be more fully understood by reference to the following examples, which are intended to illustrate the invention but not to limit its scope. All literature and patent citations are expressly incorporated by reference.

EXAMPLE I

In this example, IGF-I was periplasmically secreted from *E. coli* and purified. The recovery process is shown in FIG. 1. Upstream recovery included solubilization of IGF-I and two-phase separation that removes cell debris and partially purifies the IGF-I from bacterial protein. The downstream recovery process included protein folding and chromatography. Four chromatographic purification steps were employed: Acid C4 (reverse phase chromatography at low pH), SP-SEPHAROSE™, reverse phase HPLC, and S-SEPHAROSE™. Acid C4 purification clears aggregate and misfolded variants (where the disulfide bonds at positions 47–52 and 48-6 are reversed). SP-SEPHAROSE™ clears misfolded variant and solvent, and HPLC clears met$^{59}$O variant, two clipped forms that have either an N-terminal glycine or glycine-proline missing (desGly$^1$ and desGly$^1$Pro$^2$variants), and carbamylated variants. For more information on carbamylation, see Qin et al., *J. Biol. Chem.*, 267: 26128–26133 (1992).

The HPLC step is the last high-resolution purification step, and so purity is a prime consideration. The HPLC step here is designed to have pools with less than 2% met$^{59}$O variant and less than 2% misfolded variant.
Materials and Documentation Prepacked 1-cm diameter KROMASIL™ columns and bulk KROMASIL™ media were obtained from BTR Separations (Wilmington, DE) or from Eka-Nobel, and VYDAC™ 0.46 cm diameter prepacked KROMASIL™ columns were obtained from Phenomenex (Torrance, Calif.). Analytical columns were obtained from Phenomenex. HPLC-grade acetonitrile and isopropanol used for analysis were obtained from Baker. HPLC load material of partially purified recombinant IGF-I from bacterial fermentation was obtained as described in U.S. Pat. No. 5,446,024 through the step just before the RP-HPLC step, namely, host cell strain 37D6 and IGF-I expression plasmid pBKIGF2B (described in the '024 patent) were constructed, the host cell was transformed with the plasmid, the host cell was fermented, the IGF-I was subjected to in-situ solubilization, the IGF-I was then extracted via aqueous two-phase liquid-liquid extraction, the IGF-I was precipitated and then refolded using propylene glycol rather than ethanol, then the IGF-I was subjected to acid C-4 chromatography using hexylene glycol rather than ethanol, which involved column preparation, sample preparation and loading, and a wash and elution step, and finally, just prior to the HPLC step, cation-exchange chromatography on SP-SEPHAROSE™, in which the IGF-I was eluted with 200 mM citrate buffer, pH 6. The in situ solubilization and two-phase separation steps are also described in Hart et al., *Bio/Technology*, 12: 1113–1117 (1994).

Bulk amounts of purified met$^{59}$O variant were obtained from side fractions from purification by HPLC. Bulk amounts of purified misfolded IGF-I were obtained from side fractions from purification by SP-SEPHAPOSE™. Hexylene glycol was NF grade from Ashland Chemical (Newark, Calif.). The BioCAD™ instrument was from PerSeptive Biosystems (Framingham, Mass.), the HP0190 HPLC was from Hewlett-Packard (Mountain View, Calif.), the Delta-prep™ was from Waters (Milford, Mass.), and the PROCHROM DAC™ column and HPLC were from Prochrom USA (Indianapolis, ID).
Analytical Chromatography The VYDAC™ assay used a VYDAC™ 4.6×250 mm C18 (5 $\mu$m 300 angstrom) column at 2 ml/min, a 10-microgram injection, and detection at 214 nm. Buffer A was 0.12% trifluoroacetic acid in water, and buffer B was 0.1% trifluoroacetic acid in acetonitrile. The method was: 27.5–28.5% B/9 min, 28.5–40% B/4 min, 40–90% B/2 min, hold 90% B for 1 min, 27.5% B for 4 min. FIG. 2 shows a chromatogram for the VYDACT™ method.
Preparative Chromatography Experiments to characterize the preparative separation all used 100 mM K$_2$HPO$_4$ pH 7.0 and KROMASIL™ 1 cm diameter (10 $\mu$m, 150 angstrom) C4 columns. In general, columns were equilibrated with about 10% hexylene glycol in 100 mM K$_2$HPO$_4$ pH 7.0 for at least 3 CV, and were regenerated with at least 25% hexylene glycol or 100% B for at least 2 CV. Fractions were collected throughout the elution and analyzed by the VYDAC™ assay. Load material had 10% met$^{59}$O variant as determined by the VYDAC™ assay. Chromatography was performed on a BioCAD™ device.

Flow rate experiments used a 25-cm-length column at 30° C. loaded to 3 mg IGF-I/ml CV with a gradient from 14.25–15.75% hexylene glycol over 15 CV at flow rates of 50, 75, 150, 225, 300, and 400 cm/hr. Load experiments used a 25-cm-length column at 30° C. at a flow rate of 255 cm/hr with a gradient from 12.5–15.5% hexylene glycol over 15 CV at loads of 3, 9, 17, and 26 mg IGF-I/ml CV. Temperature experiments used a 25-cm-length column at a flow rate of 255 cm/hr loaded to 3 mg IGF-I/ml CV with a gradient from 12.5–17.5% hexylene glycol over 15 CV at temperatures of 30, 50, 65, and 80° C. Column length experiments used a temperature of 50° C. with a gradient of 10–15% hexylene glycol/22 CV and column lengths of 10, 15, 25, 40, and 50 cm at flow rates of 520, 420, 400, 300, and 200 cm/hr, respectively. Gradient slope experiments used a 25-cm-length column at 30° C. with a flow rate of 255 cm/hr loaded to 3 mg IGF-I/ml CV with a gradient from 12.5–22.5, 12.5–17.5, 14–17, 14.25–15.75% hexylene glycol over 15 CV. For incubation experiments, a 25-cm-length column was loaded to 10 g/L and incubated for 0, 60, or 120 minutes at a flow rate of 5.25 ml/min at 50° C., then eluted with 20% hexylene glycol.

Residence time experiments used a 1×25 cm KROMA-SIL™ C4 (10 μm, 150 angstrom) column loaded to 10 mg IGF-I/ml CV with material that was adjusted to pH 7.0 and had 9% hexylene glycol added. The flow rate was 5.25 ml/min, and the column temperature was 50° C. Buffer A was 100 mM $K_2HPO_4$ pH 7.0, and Buffer B was 100 mM $K_2HPO_4$ pH 7.0/30% hexylene glycol. The column was loaded to 10 mg/ml, incubated while flowing at equilibration conditions for 0, 60, or 120 minutes, then eluted with a step to 60% B. Fractions were collected and analyzed by the VYDAC™ assay. Chromatography was run on a BioCAD/20™ apparatus.

Scale-up experiments were done on a 6×25 cm KROMA-SIL™ C4 (10 μm, 150 angstroms) media packed in a PROCHROM™ DAC column. Details of column operation are in Godbille and Devaux, *J. Chromatographic Science*, 12: 564–569 (1974). Chromatography was run on a Waters DELTA-PREP™ HPLC or PROCHROM™ HPLC system. Buffer A was 55 mM $K_2HPO_4$ 45 mM $KH_2PO_4$ pH 7.0 and Buffer B was 55 mM $K_2HPO_4$ 45 mM $KH_2PO_4$ pH 7.0/30% hexylene glycol. The method was: equilibration for 3 CV at 30% B, load 10 mg IGF-I/ml CV (9% hexylene glycol in load), wash for 1 CV at 30% B, gradient 40–50% B over 10 CV, regenerate for 1 CV at 80% B. The column was run at 400 cm/hr, or 170 ml/min, at 50° C. For misfolded variant clearance study, load was spiked with purified misfolded variant. For the peak-cutting study, load was spiked with purified met$^{59}$O variant.

Results and Discussion

FIG. 3 shows a chromatogram from the HPLC process using elution with acetonitrile. The conditions used for FIG. 3 were flow rate: 1 liter/min, column: 15×50 cm KROMA-SIL™ (10 μm, 150 angstrom) C4 packed in PROCHROM DAC™ column, temperature: 50° C., load: 20 mg IGF-I/ml CV, buffer A: 100 mM $K_2HPO_4$ pH 7.0/20% acetonitrile, buffer B: 100 mM $K_2HPO_4$ pH 7.0/40% acetonitrile, method: equilibrate 3 CV 25% B, gradient 33–36% B over 10 CV, regenerate 2 CV 80% B. Total run time is 155 minutes. Average recovery yield was 80% by the VYDAC™ assay, and throughput was 0.3 g hr$^{-1}$ cm$^{-2}$.

Mobile-phase buffer, column media, and eluent strongly affected reversed-phase separations. To keep the separation conditions as close as possible to the conditions used for acetonitrile, the nonflammable solvent separation used 100 mM potassium phosphate at pH 7.0 and KROMASIL™ 10-μm, 150-angstrom C4 media. The nonflammable solvent hexylene glycol replaced acetonitrile. IGF-I and KROMA-SIL™ were stable in the buffer, pH 7 generated good separations, and IGF-I was stable in hexylene glycol. KROMASIL™, a spherical monodisperse media, produces high-efficiency columns when packed by dynamic axial compression (Sarker and Guiochon, *J. Chromatography*, 709: 227–239 (1995), and Stanley et al.,*J. Chromatography*, 741: 175–184 (1996)), and C4 generally produces good protein separations (Nice et al., *J. Chromatography*, 218: 569–580 (1981)).

Using these conditions, a series of studies focused on developing a nonflammable HPLC process with yield, purity, and throughput equivalent to HPLC purification using elution with acetonitrile.

With preparative loads, very shallow or even isocratic gradient conditions do not produce baseline resolution of IGF-I from early-eluting variants, so separation efficiency measurement used a method that does not rely on baseline resolution. The method measured the separation of met$^{59}$O variant from IGF-I because met$^{59}$O variant must be reduced to less than 2%, met$^{59}$O variant is easy to assay, and purified met$^{59}$O variant was readily available. Met$^{59}$O variant separation is not an absolute measure of overall separation performance, but measures relative separation efficiency to compare process variables.

Separation efficiency was calculated as yield at constant purity. Fractions of the eluted preparative HPLC peak were analyzed by the VYDAC™ assay to determine the concentration of IGF-I and met$^{59}$O variant in each fraction. The results from individual fractions were summed and yield was calculated by Equation 1:

$$\text{yield} = \frac{(IGF\text{-}I \text{ in a pool with less than 1\% met}^{59}\text{O variant})}{(\text{total } IGF\text{-}I \text{ eluted})} \quad (1)$$

This yield calculation takes into account only eluted IGF-I, as opposed to loaded IGF-I, and corrects for effects (such as protein aggregation on the column) that may reduce the total IGF-I recovered but do not affect the separation of IGF-I from met$^{59}$O variant. Setting a limit of 1% met$^{59}$O variant ensured that the separation can meet the requirement of less than 2% met$^{59}$O variant.

Identifying the most preferred process was enabled by determining the effect of load, flow rate, gradient slope, temperature, and column length on separation efficiency. Each condition was varied while holding the others constant to evaluate the effect of each condition independently (the column length study had varying flow rates—higher flow rates for shorter columns—but elution yield is independent of flow rate so the results would be the same regardless of flow rate).

The results of the study are shown in FIG. 4, which provides a quantitative evaluation of the effect of flow rate (FIG. 4A), load (FIG. 4B), gradient slope (FIG. 4C), temperature (FIG. 4D), and column length (FIG. 4E) on relative separation efficiency. All experiments used 1-cm diameter KROMASIL™ (10 μm, 150 angstrom) C4 columns, 100 mM potassium phosphate, pH 7.0, and elution with hexylene glycol. The Y-axis on all graphs is yield at constant purity calculated by Equation 1. Linear fit is shown for reference only. Maximum elution yield varied among studies because the chromatographic conditions used for each study were different.

In FIG. 4, the slope of the line indicates the proportionate effect of each process condition. The results correspond well with HPLC theory. Because preparative reversed-phase HPLC of proteins is based primarily on adsorption/desorption (Geng and Regnier, *J. Chromatography*, 296: 15–30 (1984)), especially for C4 columns (Tan et al., *J. Chromatography*, 775: 1–12 (1997)), flow rate and column length (Chen and Horvath, *J. Chromat. A.*, 705: 3–20 (1995)) have little effect on chromatographic separation. High load decreases resolution (Dwyer, *Recent Advances in Separation Techniques III*, 82: 120–127 (1986)) and separation efficiency because preparative loading isotherms are nonlinear, producing overlapping peaks at high loads. Gradient slope affects separation efficiency (Jandera et al., *J. Chromatog. A*, 760: 25–39 (1997)) by changing the relative retention values for each peak (Stadalius et al., *Journal of Chromatography*, 327: 93–113 (1985)).

Preparative reversed-phase HPLC of proteins is often carried out using linear gradient elution (Lee et al., *J. Chromat.*, 443: 31–43 (1988)), primarily because it generally provides a faster separation than isocratic elution (Snyder et al., *Analytical Chemistry*, 55: 1412–1430 (1983)). Linear gradient elution is the only elution technique investigated here, where gradient slope had a noticeable effect on elution yield. Because temperature increases protein diffusivity and decreases mobile-phase viscosity, enhancing the protein's kinetic and transport properties (Antia and Horvath, *J. Chromatography*, 435: 1–15 (1988)), temperature increases separation efficiency (Yang et al., *J. Chromatog.*, 590: 35–47 (1992)). In summary, separation efficiency is unaffected by flow rate or column length, it is slightly affected by temperature and gradient slope, and it is highly affected by load.

As load increased, met$^{59}$O variant was pushed to the front of the IGF-I peak, an effect shown in FIGS. 5A to 5D that is characteristic of sample displacement behavior. In sample displacement chromatography, the weaker interacting protein is pushed forward of the stronger interacting protein, and one protein acts as a displacer for the other (Hodges et al., *J. Chromatography*, 548: 267–280 (1991)). If the displacement effect is strong enough, it can become more significant than desorption caused by gradient elution. McDonald and Bidlingmeyer, Strategies for Successful Preparative Liquid Chromatography, in *Preparative Liquid Chromatography* (Elsevier Science Publishing: New York, 1987), pp. 1–104. A distinct met$^{59}$O variant tailing occurs and the stringent requirement of less than 1% met$^{59}$O variant in the elution yield calculation gives the tailing a strong effect on elution yield. Even at low loading levels, sample displacement is still occurring, so the separation is always dependent to some extent upon sample displacement.

The column length study demonstrated that the separation is unaffected by column length, but a detailed analysis of data from the study revealed that as the column length increased, regeneration peaks became larger while the total mass of IGF-I eluted became smaller, and at longer column lengths the IGF-I pools contained higher levels of misfolded material, a variant where disulfide bonds are improperly formed (Forsberg et al., *Biochem. J.*, 271: 357 (1990); Canova-Davis et al., *Biochem. J.*, 285: 207–213 (1992)). As the column length increased, the residence time of the protein on the column increased as well. Both IGF-I loss and increased misfolded variant were linearly related to the protein residence time.

To study the effect of protein residence time quantitatively, IGF-I was incubated on the column at increasing residence times, shown in FIG. 6A. This study determined that misfolded variant forms on the column at a rate of 0.009% per minute, a rate that is about 150 times slower in the purified pool at 50° C., and is even slower in the pool at room temperature or 4° C. (determined by incubating pool material and analyzing it by the VYDAC™ assay for misfolded variant formation). By keeping the protein's residence time on the column low, the formation of misfolded variant was minimized.

For obtaining the preferred process, four interdependent goals were considered. (1) Purity: must reduce met$^{590}$ variant to less than 2%. (2) Yield: recovery yield greater than 80%. (3) Throughput: 0.3 g hr$^{-1}$ cm$^{-2}$. (4) Robustness: the process must be immune to small changes in feed stock, buffer preparation, gradient making, and load, and the process must be able reliably to collect a pure peak with no fraction collection.

Although misfolded variant is cleared by two other chromatography steps in the IGF-I process used in this example (one before and one after the HPLC step), ideally the HPLC process should not generate misfolded variant, so protein residence time is an important consideration when choosing column length, flow rate, temperature, and gradient volume. A temperature of 50° C. produced low viscosity and back pressure but still ensured stability of IGF-I, which could be compromised at higher temperature. At 400 cm/hr the column back pressure for a 25-cm length column at equilibration was 700 psi, a value that is within a large margin of safety of the PROCHROM™ column's 1000 psi maximum. Although a column shorter than 25 cm will produce less protein residence time, 25-cm length columns provided robust separations during HPLC development, and shorter columns can be difficult to pack homogeneously in PROCHROM™ DAC columns. Guiochon et al., *J. Chromatog. A*, 762: 83–88 (1997). A gradient from 12–15% hexylene glycol over 10 CV provided a shallow gradient slope while keeping the process immune to small changes in buffer production. A load of 10 mg IGF-I/ml CV produced adequate yield while maintaining a high throughput. The load material was conditioned with 9% hexylene glycol prior to loading. A mixture of monobasic and dibasic potassium phosphate gave 100 mM buffer at pH 7.0 with no pH adjustment.

A chromatogram using the scale-up conditions on a 6-cm diameter column is shown in FIGS. 7A and 7B. FIG. 7A shows a chromatogram from the HPLC process using hexylene glycol elution on the 6-cm-diameter column and scale-up conditions as described herein. Pool lines indicate cut for less than 1% met$^{59}$O variant. The total run time was 65 minutes, but it could be reduced to 50 minutes by beginning regeneration immediately after pooling ends. Inset (FIG. 7B) is the preparative peak with variants shown as determined by the VYDAC™ assay.

The method is able to clear some misfolded variant, an effect shown in FIG. 6B. Increasing amounts of misfolded variant added to the load, and the load and pool were analyzed by the VYDAC™ assay to find misfolded variant levels in a pool with less than 1% met$^{59}$O variant. Equation of the line is y=0.1+0.85x, R=0.995. With a slope of 0.85, there is 15% reduction of misfolded variant.

Because the process does not provide baseline resolution between IGF-I and early-eluting variants, and collecting fractions is undesirable for production, the process needs a method to cut the peak accurately based on UV absorbance. The specific amount of each variant in the load can change from batch to batch. The separation of met$^{59}$O variant from IGF-I was used to model changing variant levels by spiking increasing amounts of purified met$^{59}$O variant into load pools.

FIGS. 8A–8D show the results of the peak-cutting study. Load material was spiked with purified met$^{59}$O variant and run on a 6-cm-diameter column. As the amount of met$^{59}$O variant in the load increased, the met$^{59}$O variant peak was displaced further out in front of the IGF-I peak, which means that in order to remove increased amounts of met$^{59}$O variant, more of the preparative peak must be cut away. By 75% peak height, most of the met$^{59}$O variant had finished eluting, and a pool that began at 75% peak height contained less than 1% met$^{59}$O variant at all met$^{59}$O variant levels, indicating that at 75% peak height pooling can begin regardless of the variant content. At 10 g/L load the height of the IGF-I peak is reproducibly 7 g/L, so the peak height at 280 nm can be predicted in advance for any UV monitor by detector calibration.

Routine manufacturing requires column cycling. FIG. 9 shows the results of column cycling using the 6-cm-diameter column and scale-up conditions described herein. Pools were collected from 75% to 25% peak height. Four different load materials were used, with 11 cycles of load 1, five cycles of load 2, 19 cycles of load 3, and 32 cycles of load 4. The variant content in the load was typical of the GMP production pools. In FIG. 9, pool values are averages, and error bars are one standard deviation. On average, the goal of less than 1% met$^{59}$O variant was accomplished, with variations of 3–6% met$^{59}$O variant in the load. Throughput was 0.3 g hr$^{-1}$ cm$^{-2}$, and average recovery yield was greater than 80% by the VYDAC™ assay. The process is robust enough to sustain routine manufacturing, and pure IGF-I can be reliably pooled.

SUMMARY

The nonflammable HPLC process uses a direct replacement of hexylene glycol for acetonitrile—the column, buffer, and temperature remain the same. A quantitative evaluation of how processing parameters affect separation efficiency enabled scale-up maximization. Variants can be removed while maintaining an average recovery yield greater than 80% and a throughput of 0.3 g hr$^{-1}$ cm$^{-2}$ in a robust, reliable process.

After the IGF-I is purified by RP-HPLC, it may then be loaded on an S-SEPHAROSE™ column to remove solvent as set forth in U.S. Pat. No. 5,446,024 and formulated using tangential flow filtration (U.S. Pat. Nos. 5,256,294 and 5,490,937) for diafiltration to place IGF-I into the buffer desired for formulation, such as citrate or acetate buffer, with one preferred type of formulation described in copending U.S. Ser. No. 08/071,819 filed Jun. 4, 1993, to be issued as U.S. Pat. No. 5,681,814 on Oct. 28, 1997.

EXAMPLE II

Three separations of model compounds demonstrate the wide applicability of hexylene glycol as a reversed-phase eluent. The separation of model proteins, e.g., chicken egg proteins (lysozyme from ovalbumin), peptides (substance P from bradykinin), and hormones (hydrocortisone from progesterone) is often used to characterize the behavior of new chromatography methods (Li and Spencer, *J. Biotechnol.*, 26: 203–211 (1992); Kenney, *Methods Mol. Biol.*, 11: 249–258 (1992); Sands et al., *J. Chromatogr.*, 360: 353–369 (1986); Levison et al., *J. Chromatogr. A*, 734: 137–143 (1996); Wei et al., *Biomed. Chromatogr.*, 4: 34–38 (1990); Buckle, *J. Physiol.*, 242: 56P–57P (1974)).

Purified forms of each compound were obtained from Sigma (St. Louis, Mo.). The elution position of each compound was confirmed by injecting each compound individually. The compounds are described in Table 1 (information from the Merck Index).

All separations used two mobile phases: A was 0.1% TFA (v/v) in water and B was 0.1% TFA (v/v) in 60% hexylene glycol/40% water (v/v). All separations used a 4.6 mm×150 mm VYDACT™ 10 micron C4 column, a column temperature of 50° C., and a flow rate of 1.25 ml/min. The separation of lysozyme from ovalbumin and the separation of progesterone from hydrocortisone both used a gradient from 10–100% B over 10 column volumes, and detected peaks using absorbance at 280 nm. The separation of substance P from bradykinin used a gradient from 8–70% B over 10 column volumes, and detected peaks using absorbance at 214 nm.

All separations were performed using preparative loads. The separation of lysozyme from ovalbumin was accomplished using an injection of 0.25 ml of a solution of approximately 10 g/L lysozyme and 5 g/L ovalbumin in 0.1% TFA/10% hexylene glycol/90% water (v/v), for a total protein load of 1.5 g protein/L column volume. The separation of substance P from bradykinin was accomplished using an injection of 0.25 ml of a solution of approximately 10 g/L substance P and 0.5 g/L bradykinin in 0.1% TFA/20% hexylene glycol/80% water (v/v), for a total load of approximately 1 g peptide/L column volume. The separation of hydrocortisone from progesterone was accomplished using a 0.25 ml injection of approximately 10 g/L hydrocortisone and 5 g/L progesterone in 0.1% TFA/40% hexylene glycol/60% water (v/v), for a total load of 1.5 g hormone/L column volume.

The separations are shown in FIGS. 10A (lysozyme and ovalbumin), 10B (bradykinin and Substance P), and 10C (hydrocortisone and progesterone). It is clear from the results that hexylene glycol is useful as a reversed-phase eluent for a wide range of separations.

EXAMPLE III

The preparative reversed-phase liquid chromatography performance can be modeled using analytical separations (Cox and Snyder, LC-GC, 6: 894 (1988), and Snyder et al., *Practical HPLC Method Development* (Wiley-Interscience: New York, 1988)). To determine a preferred eluent, three nonflammable solvents were compared to acetonitrile for their ability to separate met$^{59}$O variant from IGF-I by injecting 10 μg of a mixture of 20% met$^{59}$O variant/80% IGF-I onto a VYDAC™ 5-μm 90-angstrom C18 column in 100 mM K$_2$HPO$_4$ pH 7.0 and 2.2. Isocratic conditions were found where the retention time of IGF-I was approximately 12 minutes on an HP1090™ chromatograph. Resolution was calculated as $$R_s = 2 \times \{(t_2 - t_1)/(W_1 + W_2)\},$$

where $R_s$ is resolution, $t_1$ and $t_2$ are the retention times of met$^{59}$O variant and IGF-I, respectively, and $W_1$ and $W_2$ are

TABLE 1

|  | pI | Molecular Weight | Notes |
| --- | --- | --- | --- |
| Lysozyme | 10.5 | 14,400 | Single polypeptide chain of 129 amino acids and four disulfide bonds. |
| Ovalbumin | 4.63 | 45,000 | Single polypeptide chain of about 400 amino acids (about half are hydrophobic), two phosphate residues per mole, and a saccharide side chain. |
| Bradykinin |  | 1060.25 | Arg-Pro-Pro-Gly-Phe-Ser-Pro-Phe-Arg (SEQ ID NO:1) |
| Substance P |  | 1347.66 | Arg-Pro-Lys-Pro-Gln-Phe-Phe-Gly-Leu-Met (SEQ ID NO:2) |
| Hydrocortisone |  | 362.47 | $C_{21}H_{30}O_5$ |
| Progesterone |  | 314.45 | $C_{21}H_{30}O_2$ | the peak widths (in units of time) of met$^{59}$O variant and IGF-I, respectively. Resolution is a unitless measure.

The results of the study are shown in FIG. 11. Resolution was determined for four eluents at 2 pH values. At pH 7.0, acetonitrile had the highest resolution of met$^{59}$O variant and IGF-I, and of the nonflammable solvents, hexylene glycol had the highest resolution. At pH 2.2, acetonitrile had only slightly better resolution than hexylene glycol, which is still the best nonflammable solvent in this study.

EXAMPLE IV

Several C4 columns were screened by loading 3.5 mg IGF-I/ml CV. All columns were 1×25 cm and were run at 30° C. Buffer A was 100 mM K$_2$HPO$_4$ pH 7.0, and Buffer B was 100 mM K$_2$HPO$_4$ pH 7.0/50% hexylene glycol. A gradient was run from 25 to 45% B over 15 CV at 3 ml/min. Chromatography was run on a BioCAD/20™ column. Fractions were analyzed by using a VYDAC™ column, and yield was calculated by Equation 1.

FIG. 12 shows the results of this study. Columns of different particle and pore size gave separation of IGF-I and met$^{59}$O variant, demonstrating that this separation could be carried out on a wide range of chromatography media. A small number of columns had zero yield, where no eluted fractions had less than 1% met$^{59}$O variant. As indicated by the results from the IMPAQ™ resins, there is a strong correlation between particle size and separation efficiency, another indication that hexylene glycol acts the same as any traditional eluent. The KROMASIL™ column provides one of the highest separation efficiencies in this study.

EXAMPLE V

Hexylene glycol has a high viscosity, but in aqueous solutions its viscosity drops sharply, and is highly affected by temperature. FIG. 13 shows viscosity determined by a disk viscometer as a function of hexylene glycol concentration at three different temperatures. The viscosity of hexylene glycol has a greater temperature dependence than acetonitrile (Chen and Horvath, *Analytical Methods and Instrumentation*, 1: 213–222 (1993)), allowing it to be useful for reversed-phase chromatography.

EXAMPLE VI

Hexylene glycol is useful for low-pressure reversed-phase chromatography of IGF-I. An example of a separation using this chromatography at acidic pH is shown in FIGS. 14A-1 and 14A-2. Conditions for this separation were: Column: 1.4 m×32 cm BAKERBOND™ C4 (40 μm, 275 angstrom), A: 50 mM acetic acid, 50 mM citric acid, pH 3.0; B: 50 mM acetic acid, 20 mM citric acid, pH 3.0, 50% hexylene glycol; temperature: 22° C., flow: 5 CV/hr, load: 18 g IGF-I/L CV. The method used was to equilibrate 3 CV 100% A, load with a gradient of 10–40% B over 10 CV, and regenerate 2 CV 100% B. Fractions were collected and analyzed by the VYDAC™ assay; the results of this analysis are shown in the inset FIG. 14A-2.

This separation works over a wide range of load, temperature, and gradient slope. Methods to determine this were: Column: 1×25 cm (20 ml) BAKERBOND™ C4 (40 μm, 275 angstrom), A: 50 mM acetic acid, 50 mM citric acid, pH 3.0; B: 50 mM acetic acid, 20 mM citric acid, pH 3.0; 50% hexylene glycol; load: gradient study: 12.5 mg IGF-I/ml CV; load study: 5, 8.5, 12.5, 15 mg IGF/ml CV; temperature: 30° C.; flow: equilibrate/load/wash at 20 CV/hr; gradient/regenerate at 9 CV/hr. The method used was to equilibrate 3 CV 100% A, load, wash 2 CV 100% A, gradient: load study: 0–50% B/10 CV, gradient study: 0–50% B/6.5, 10, 15, 20 CV, and regenerate 2 CV 100% B. The pool was analyzed by the VYDAC™ assay. The load by VYDAC™ was 38.4% IGF-I, 43.0% aggregate, 7.5% misfolded variant, and 9.1% met$^{59}$O variant.

The results of these studies are shown in FIGS. 14B and 14C. It is seen that over a wide range of conditions, yield and purity remain essentially constant for low-pressure reversed-phase liquid chromatography of IGF-I at low pH.

What is claimed is:

1. A process for purifying a polypeptide comprising loading a mixture containing the polypeptide onto a reversed-phase liquid chromatography column and eluting the polypeptide from the column with a buffer containing hexylene glycol.

2. The process of claim 1 wherein the polypeptide is selected from the group consisting of growth factors, thrombopoietin, hormones, chicken egg proteins, peptides of 5–25 amino acids, antibodies or antibody fragments, and proteins that bind to hormones or growth factors.

3. The process of claim 2 wherein the growth factor is an insulin-like growth factor.

4. The process of claim 3 wherein the hexylene glycol is at a concentration of about 10–15% (v/v).

5. The process of claim 4 wherein the column is a high-performance liquid chromatography column.

6. The process of claim 1 wherein the column is a high-performance liquid chromatography column.

7. The process of claim 1 wherein the hexylene glycol is at a concentration of about 10–40% (v/v).

8. The process of claim 1 wherein the buffer is at a pH of about 2.5 to 8.

9. The process of claim 8 wherein the pH is about 2.5–5.

10. The process of claim 8 wherein the pH is about 6–7.5.

11. The process of claim 1 wherein the column is packed with a medium having a particle diameter of about 10–40 microns and a C4–C18 alkyl group.

12. The process of claim 1 wherein the column is a preparative column.

13. The process of claim 12 wherein the column has a diameter of at least about 1 cm or the molecule is loaded in an amount of at least about 0.1 g/liter, or both.

14. The process of claim 12 wherein the column has a diameter of at least about 6 cm or the molecule is loaded in an amount of about 1 g/liter, or both.

15. The process of claim 1 further comprising loading the polypeptide-containing eluate onto a cation-exchange column and eluting the polypeptide.

* * * * *